United States Patent
Moran et al.

(10) Patent No.: US 6,949,568 B2
(45) Date of Patent: *Sep. 27, 2005

(54) ARYL ANILINE $\beta_2$ ADRENERGIC RECEPTOR AGONISTS

(75) Inventors: Edmund J. Moran, San Francisco, CA (US); John R. Jacobsen, San Mateo, CA (US); James Aggen, Burlingame, CA (US)

(73) Assignee: Theravance, Inc., South San Francisco, CA (US)

(*) Notice: Subject to any disclaimer, the term of this patent is extended or adjusted under 35 U.S.C. 154(b) by 60 days.

This patent is subject to a terminal disclaimer.

(21) Appl. No.: 10/642,926

(22) Filed: Aug. 18, 2003

(65) Prior Publication Data

US 2004/0059116 A1 Mar. 25, 2004

Related U.S. Application Data

(63) Continuation of application No. 10/292,211, filed on Nov. 12, 2002, now Pat. No. 6,653,323.
(60) Provisional application No. 60/338,194, filed on Nov. 13, 2001.

(51) Int. Cl.[7] .................... A61K 31/47; C07D 215/16
(52) U.S. Cl. .................... 514/312; 514/653; 546/157
(58) Field of Search ................ 514/312, 653; 546/157

(56) References Cited

U.S. PATENT DOCUMENTS

| | | |
|---|---|---|
| 4,894,219 A | 1/1990 | Baker et al. |
| 5,750,701 A | 5/1998 | Beeley et al. |
| 6,265,581 B1 | 7/2001 | Bell et al. |
| 6,541,669 B1 | 4/2003 | Moran et al. |
| 6,576,793 B1 | 6/2003 | Moran et al. |
| 6,653,323 B2 * | 11/2003 | Moran et al. ............... 514/312 |
| 2002/0022625 A1 | 2/2002 | Walland et al. |

FOREIGN PATENT DOCUMENTS

| | | |
|---|---|---|
| BE | 849.794 | 4/1977 |
| EP | 0 147 719 A2 | 7/1985 |
| JP | 52-83379 | 7/1977 |
| WO | WO 95/25104 A1 | 9/1995 |
| WO | WO 00/75114 A1 | 12/2000 |
| WO | WO 01/07026 A2 | 2/2001 |
| WO | WO 01/35947 A2 | 5/2001 |
| WO | WO 01/83462 A1 | 11/2001 |
| WO | WO 02/38544 A2 | 5/2002 |

OTHER PUBLICATIONS

Deyrup et al., "Structure–affinity profile of 8–hydroxycarbostyril–based agonists that dissociate slowly from the $\beta_2$–adrenoceptor", Naunyn–Schmiedeberg's Arch Pharmacol, vol. 359: pp 168–177 (1999).

Isogaya et al., "Binding Pockets of the $\beta_1$– and $\beta_2$–Adrenergic Receptors for Subtype–Selective Agonists", Molecular Pharmacology, vol. 56, pp 875–885 (1999).

Milecki et al., "Carbostyril Derivatives Having Potent $\beta$–Adrenergic Agonist Properties", vol. 30, pp 1563–1566, 1987.

Yoshizaki et al., "Sympathomimetic Amines Having a Carbostyril Nucleus", vol. 19, No. 9, pp 1138–1142 (1976).

* cited by examiner

*Primary Examiner*—D. Margaret Seaman
(74) *Attorney, Agent, or Firm*—Roberta P. Saxon; Jeffrey A. Hagenah

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

11 Claims, No Drawings

ARYL ANILINE β₂ ADRENERGIC RECEPTOR AGONISTS

CROSS REFERENCE TO RELATED APPLICATIONS

This application is a continuation of U.S. application Ser. No. 10/292,211, filed Nov. 12, 2002 now U.S. Pat. No. 6,653,323, which claims the benefit of U.S. Provisional Application No. 60/338,194, filed Nov. 13, 2001, the entire disclosures of which are incorporated herein by reference.

FIELD OF THE INVENTION

The invention is directed to novel $\beta_2$ adrenergic receptor agonists. The invention is also directed to pharmaceutical compositions comprising such compounds, methods of using such compounds to treat diseases associated with $\beta_2$ adrenergic receptor activity, and processes and intermediates useful for preparing such compounds.

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable potency, selectivity, speed of onset, and/or duration of action. Thus, there is a need for additional $\beta_2$ adrenergic receptor agonists having improved properties. Preferred agents may possess, among other properties, improved duration of action, potency, selectivity, and/or onset.

SUMMARY OF THE INVENTION

The invention provides novel compounds that possess $\beta_2$ adrenergic receptor agonist activity. Accordingly, this invention provides compounds of formula (I):

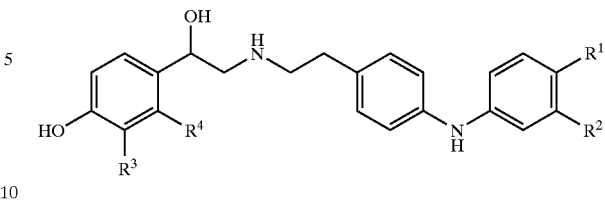

wherein:
$R^1$ is methoxy or ethoxy and $R^2$ is hydrogen or phenyl; or $R^1$ is hydrogen and $R^2$ is phenyl; and
$R^3$ is —CH₂OH or —NHCHO and $R^4$ is hydrogen; or $R^3$ and $R^4$ taken together are —NHC(=O)CH=CH—;
or a pharmaceutically-acceptable salt or solvate or stereoisomer thereof.

The invention also provides a pharmaceutical composition comprising a compound of the invention and a pharmaceutically-acceptable carrier.

The invention also provides a method of treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal, comprising administering to the mammal, a therapeutically effective amount of a compound of the invention.

The invention also provides a method of treating a disease or condition associated with $\beta_2$ adrenergic receptor activity in a mammal, comprising administering to the mammal, a therapeutically effective amount of a pharmaceutical composition of the invention.

This invention also provides a method of modulating a $\beta_2$ adrenergic receptor, the method comprising contacting a $\beta_2$ adrenergic receptor with a modulating amount of a compound of the invention.

In separate and discrete aspects, the invention also provides synthetic processes and intermediates, including compounds of formulas (V), (VI), and (IX) described herein, which are useful for preparing compounds of the invention.

The invention also provides a compound of the invention as described herein for use in medical therapy, as well as the use of a compound of the invention in the manufacture of a formulation or medicament for treating a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation) in a mammal.

Preferred compounds of the invention are shown in Table I.

TABLE I

Preferred Compounds of The Invention

| Compound | Structure |
|---|---|
| 1 | 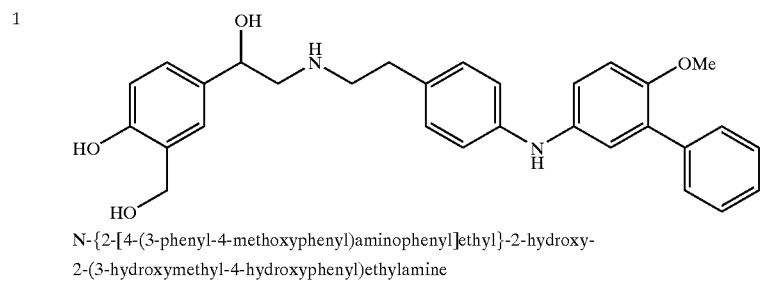<br>N-{2-[4-(3-phenyl-4-methoxyphenyl)aminophenyl]ethyl}-2-hydroxy-2-(3-hydroxymethyl-4-hydroxyphenyl)ethylamine |

TABLE I-continued

Preferred Compounds of The Invention

| Compound | Structure |
|---|---|
| 2 | 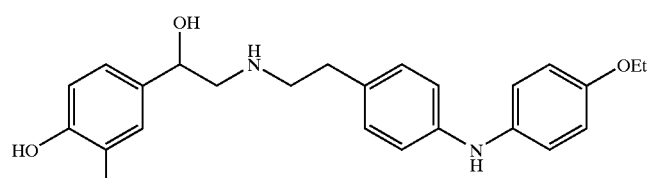
N-{2-[4-(4-ethoxyphenyl)aminophenyl]ethyl}-2-hydroxy-2-(3-hydroxymethyl-4-hydroxyphenyl)ethylamine |
| 3 | 
N-{2-[4-(3-phenylphenyl)aminophenyl]ethyl}-2-hydroxy-2-(3-hydroxymethyl-4-hydroxyphenyl)ethylamine |
| 4 | 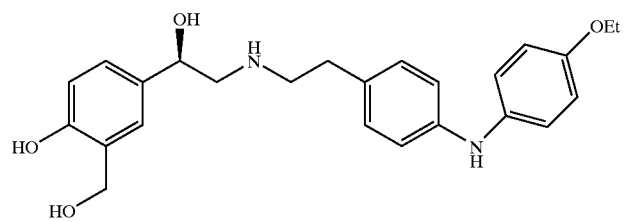
N-{2-[4-(4-ethoxyphenyl)aminophenyl]ethyl}-(R)-2-hydroxy-2-(3-hydroxymethyl-4-hydroxyphenyl)ethylamine |
| 5 | 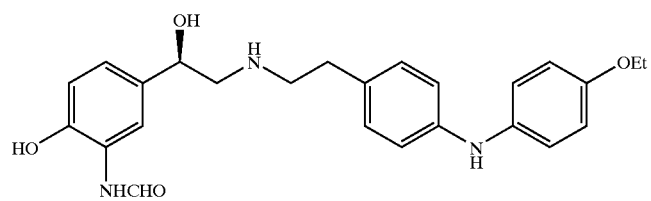
N-{2-[4-(4-ethoxyphenyl)aminophenyl]ethyl}-(R)-2-hydroxy-2-(3-formamido-4-hydroxyphenyl)ethylamine |
| 6 | 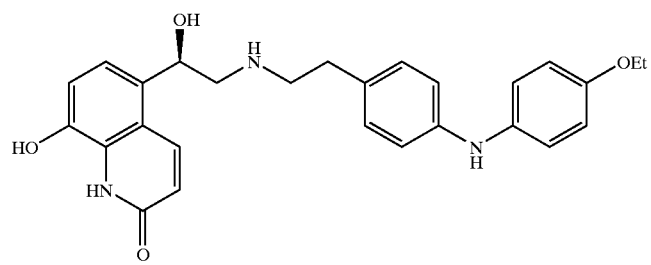
N-{2-[4-(4-ethoxyphenyl)aminophenyl]ethyl}-(R)-2-hydroxy-2-(8-hydroxy-2(1H)-quinolinon-5-yl)ethylamine |

TABLE I-continued

Preferred Compounds of The Invention

| Compound | Structure |
|---|---|
| 7 | 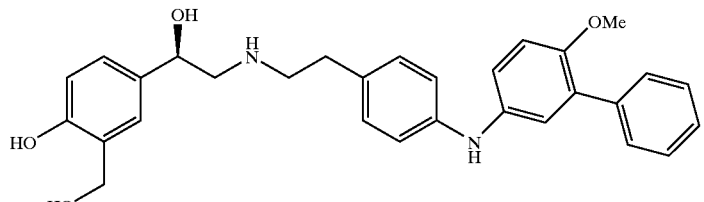<br>N-{2-[4-(3-phenyl-4-methoxyphenyl)aminophenyl]ethyl}-(R)-2-hydroxy-2-(3-hydroxymethyl-4-hydroxyphenyl)ethylamine |
| 8 | 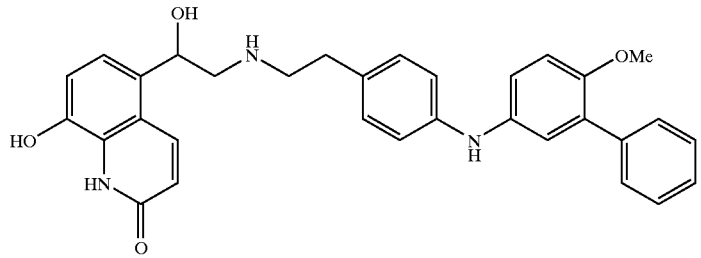<br>N-{2-[4-(3-phenyl-4-methoxyphenyl)aminophenyl]ethyl}-2-hydroxy-2-(8-hydroxy-2(1H)-quinolinon-5-yl)ethylamine |
| 9 | 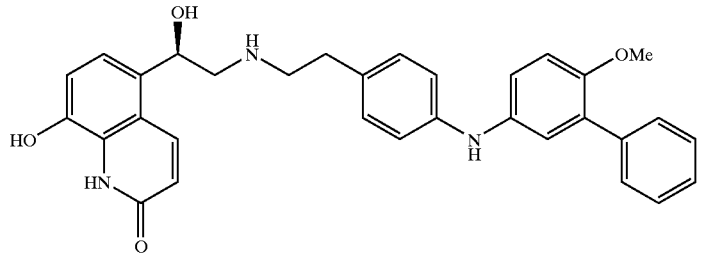<br>N-{2-[4-(3-phenyl-4-methoxyphenyl)aminophenyl]ethyl}-(R)-2-hydroxy-2-(8-hydroxy-2(1H)-quinolinon-5-yl)ethylamine |
| 10 | 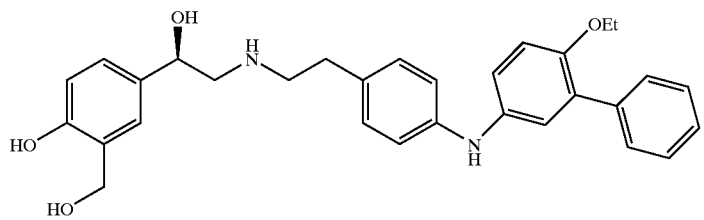<br>N-{2-[4-(3-phenyl-4-ethoxyphenyl)aminophenyl]ethyl}-(R)-2-hydroxy-2-(3-hydroxymethyl-4-hydroxyphenyl)ethylamine |
| 11 | 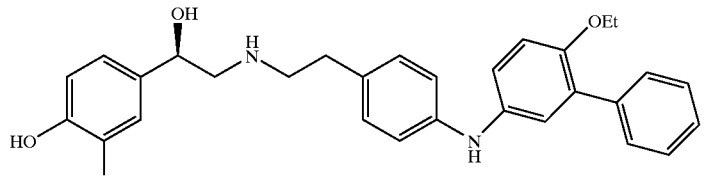<br>N-{2-[4-(3-phenyl-4-ethoxyphenyl)aminophenyl]ethyl}-(R)-2-hydroxy-2-(3-formamido-4-hydroxyphenyl)ethylamine |

TABLE I-continued

Preferred Compounds of The Invention

| Compound | Structure |
|---|---|
| 12 | 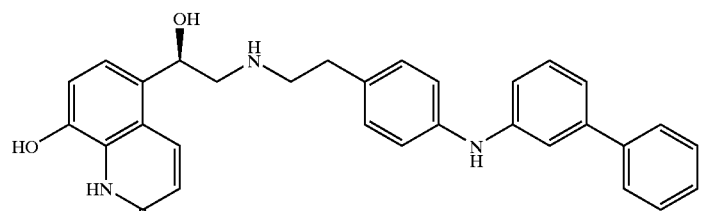<br>N-{2-[4-(3-phenylphenyl)aminophenyl]ethyl}-(R)-2-hydroxy-2-(8-hydroxy-2(1H)-quinolinon-5-yl)ethylamine |
| 13 | 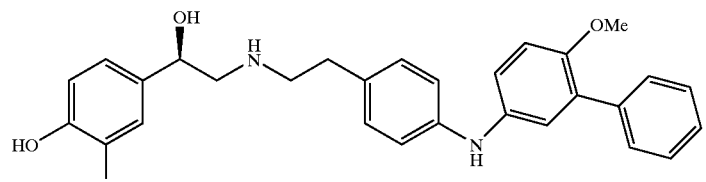<br>N-{2-[4-(3-phenyl-4-methoxyphenyl)aminophenyl]ethyl}-(R)-2-hydroxy-2-(3-formamido-4-hydroxyphenyl)ethylamine |
| 14 | 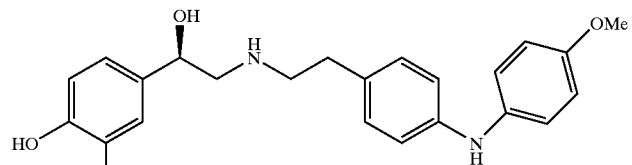<br>N-{2-[4-(4-methoxyphenyl)aminophenyl]ethyl}-(R)-2-hydroxy-2-(3-hydroxymethyl-4-hydroxyphenyl)ethylamine |
| 15 | 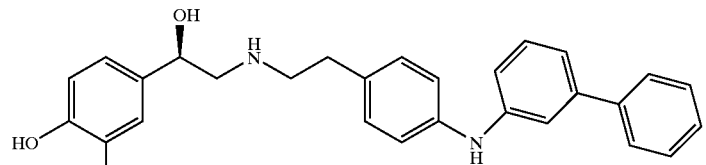<br>N-{2-[4-(3-phenylphenyl)aminophenyl]ethyl}-(R)-2-hydroxy-2-(3-hydroxymethyl-4-hydroxyphenyl)ethylamine |
| 16 | 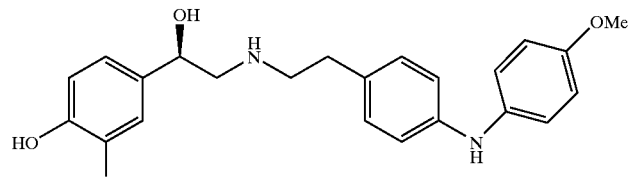<br>N-{2-[4-(4-methoxyphenyl)aminophenyl]ethyl}-(R)-2-hydroxy-2-(3-formamido-4-hydroxyphenyl)ethylamine |
| 17 | 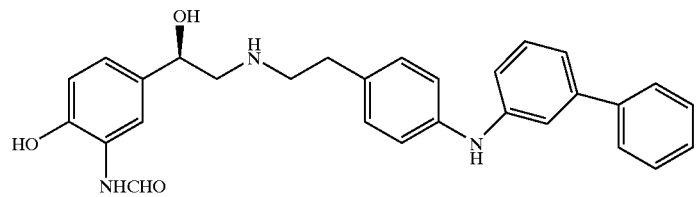 |

TABLE I-continued

Preferred Compounds of The Invention

| Compound | Structure |
|---|---|
| | N-{2-[4-(3-phenylphenyl)aminophenyl]ethyl}-(R)-2-hydroxy-2-(3-formamido-4-hydroxyphenyl)ethylamine |
| 18 | 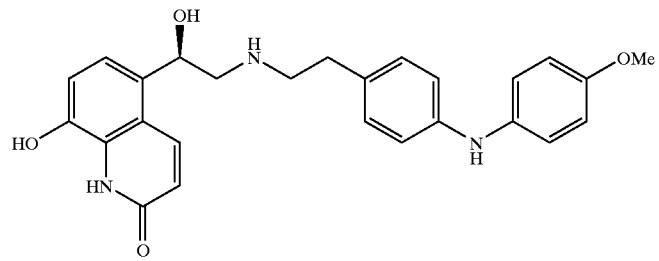 |
| | N-{2-[4-(4-methoxyphenyl)aminophenyl]ethyl}-(R)-2-hydroxy-2-(8-hydroxy-2(1H)-quinolinon-5-yl)ethylamine |
| 19 | 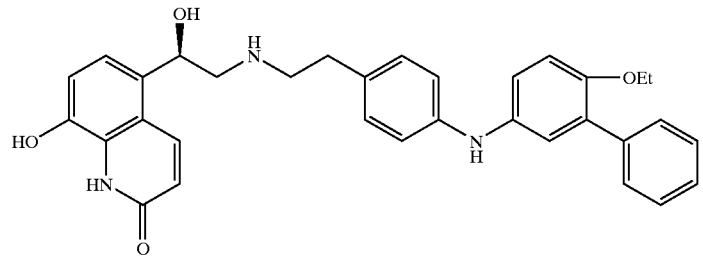 |
| | N-{2-[4-(3-phenyl-4-ethoxyphenyl)aminophenyl]ethyl}-(R)-2-hydroxy-2-(8-hydroxy-2(1H)-quinolinon-5-yl)ethylamine |
| 20 | 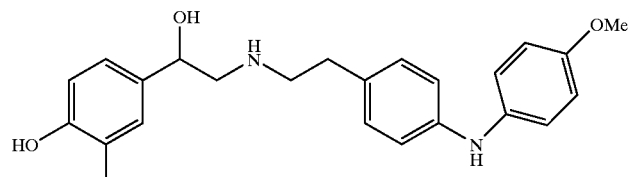 |
| | N-{2-[4-(4-methoxyphenyl)aminophenyl]ethyl}-2-hydroxy-2-(3-hydroxymethyl-4-hydroxyphenyl)ethylamine |
| 21 | 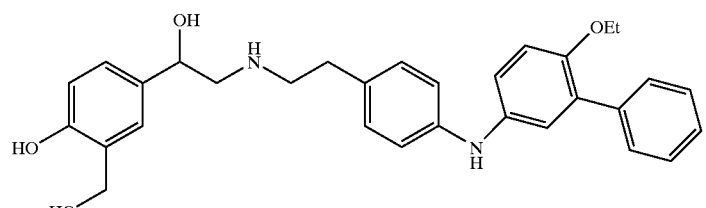 |
| | N-{2-[4-(3-phenyl-4-ethoxyphenyl)aminophenyl]ethyl}-2-hydroxy-2-(3-hydroxymethyl-4-hydroxyphenyl)ethylamine |
| 22 | 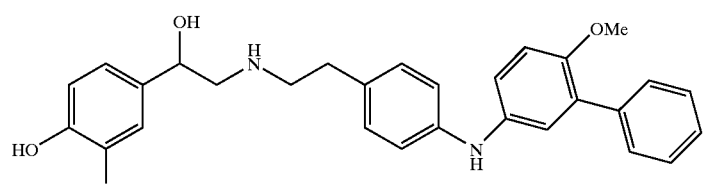 |
| | N-{2-[4-(3-phenyl-4-methoxyphenyl)aminophenyl]ethyl}-2-hydroxy-2-(3-formamido-4-hydroxyphenyl)ethylamine |

TABLE I-continued

Preferred Compounds of The Invention

| Compound | Structure |
| --- | --- |
| 23 | 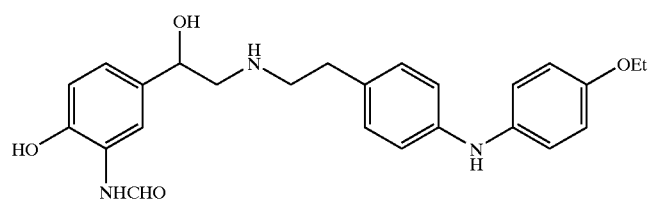
N-{2-[4-(4-ethoxyphenyl)aminophenyl]ethyl}-2-hydroxy-2-(3-formamido-4-hydroxyphenyl)ethylamine |
| 24 | 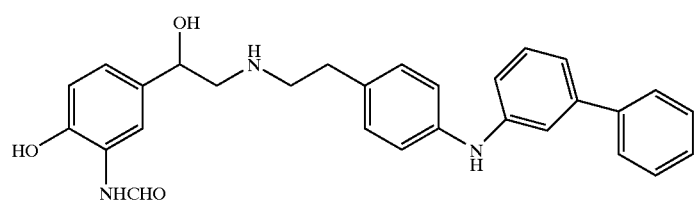
N-{2-[4-(3-phenylphenyl)aminophenyl]ethyl}-2-hydroxy-2-(3-formamido-4-hydroxyphenyl)ethylamine |
| 25 | 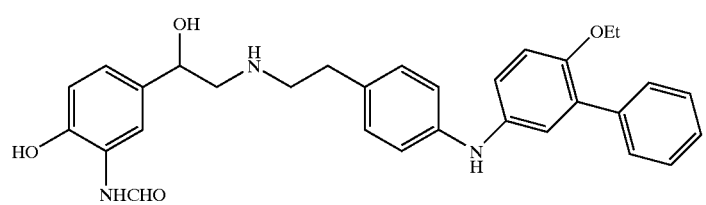
N-{2-[4-(3-phenyl-4-ethoxyphenyl)aminophenyl]ethyl}-2-hydroxy-2-(3-formamido-4-hydroxyphenyl)ethylamine |
| 26 | 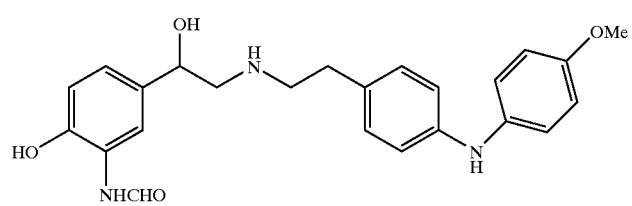
N-{2-[4-(4-methoxyphenyl)aminophenyl]ethyl}-2-hydroxy-2-(3-formamido-4-hydroxyphenyl)ethylamine |
| 27 | 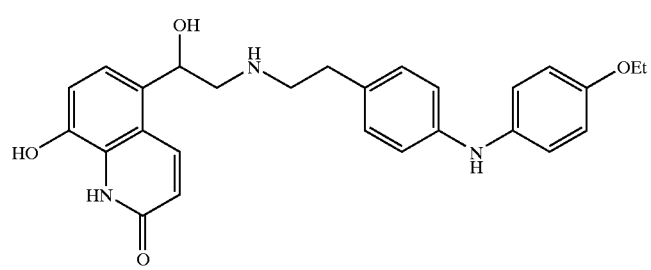
N-{2-[4-(4-ethoxyphenyl)aminophenyl]ethyl}-2-hydroxy-2-(8-hydroxy-2(1H)-quinolinon-5-yl)ethylamine |

TABLE I-continued

Preferred Compounds of The Invention

| Compound | Structure |
|---|---|
| 28 | 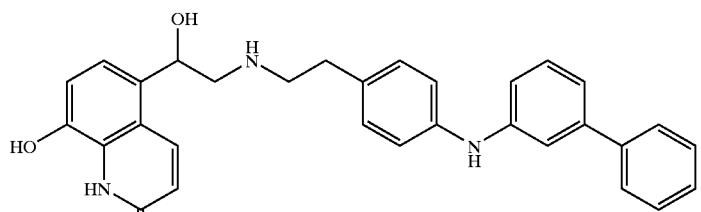<br>N-{2-[4-(3-phenylphenyl)aminophenyl]ethyl}-2-hydroxy-2-(8-hydroxy-2(1H)-quinolinon-5-yl)ethylamine |
| 29 | 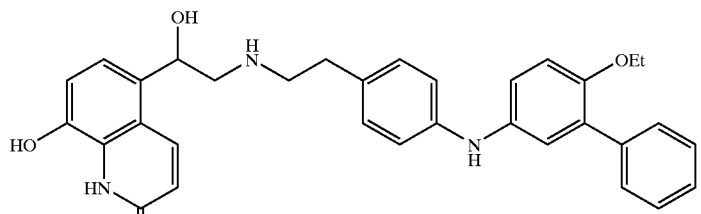<br>N-{2-[4-(3-phenyl-4-ethoxyphenyl)aminophenyl]ethyl}-2-hydroxy-2-(8-hydroxy-2(1H)-quinolinon-5-yl)ethylamine |
| 30 | 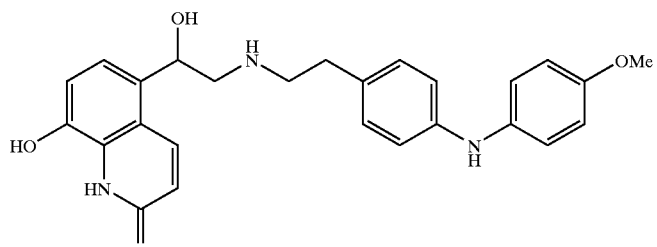<br>N-{2-[4-(4-methoxyphenyl)aminophenyl]ethyl}-2-hydroxy-2-(8-hydroxy-2(1H)-quinolinon-5-yl)ethylamine |

DETAILED DESCRIPTION OF THE INVENTION

When describing the compounds, compositions and methods of the invention, the following terms have the following meanings, unless otherwise indicated.

The term "methoxy" or "—OMe" refers to a group of the formula —$OCH_3$, and the term "ethoxy" or "—OEt" refers to a group of the formula —$OCH_2CH_3$.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, bronchoconstrictive or pulmonary diseases, such as asthma and chronic obstructive pulmonary disease (including chronic bronchitis and emphysema), as well as neurological disorders and cardiac disorders. $\beta_2$ Adrenergic receptor activity is also known to be associated with pre-term labor (see, for example, U.S. Pat. No. 5,872,126) and some types of inflammation (see, for example, WO 99/30703 and U.S. Pat. No. 5,290,815).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid) and the like. Particularly preferred are salts derived from fumaric, hydrobromic, hydrochloric, acetic, sulfuric, phosphoric, methanesulfonic, p-toluenesulfonic, xinafoic, tartaric, citric, malic, maleic, succinic, and benzoic acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "solvate" refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" refers to a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

One preferred group of compounds is the group of compounds of formula (II):

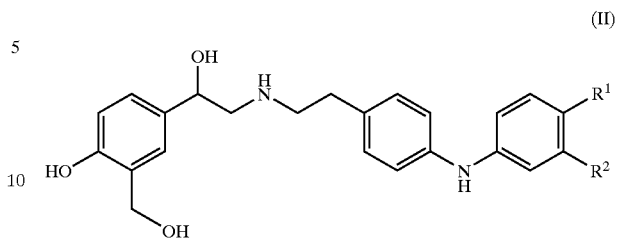

(II)

wherein $R^1$ is methoxy or ethoxy and $R^2$ is hydrogen or phenyl; or wherein $R^1$ is hydrogen, and $R^2$ is phenyl; or a pharmaceutically-acceptable salt or solvate or stereoisomer thereof.

Another preferred group of compounds is the group of compounds of formula (III):

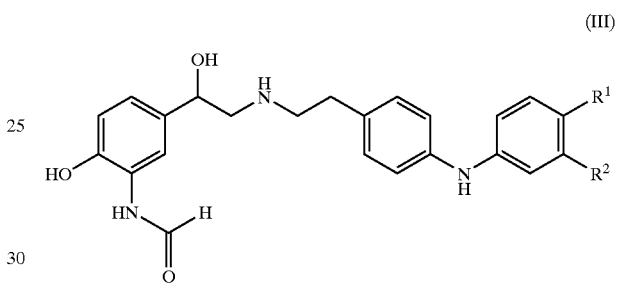

(III)

wherein $R^1$ is methoxy or ethoxy and $R^2$ is hydrogen or phenyl; or wherein $R^1$ is hydrogen, and $R^2$ is phenyl; or a pharmaceutically-acceptable salt or solvate or stereoisomer thereof.

Another preferred group of compounds is the group of compounds of formula (IV):

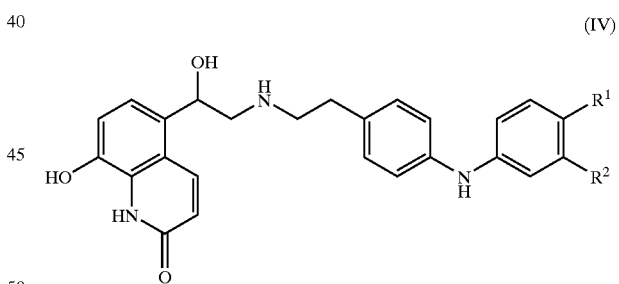

(IV)

wherein $R^1$ is methoxy or ethoxy and $R^2$ is hydrogen or phenyl; or wherein $R^1$ is hydrogen, and $R^1$ is phenyl; or a pharmaceutically-acceptable salt or solvate or stereoisomer thereof.

The compounds of the invention contain a chiral center Accordingly, the invention includes racemic mixtures, pure stereoisomers (i.e. individual enantiomers), and stereoisomer-enriched mixtures, unless otherwise indicated. When a particular stereoisomer is shown, it will be understood by those skilled in the art, that minor amounts of other stereoisomers may be present in the compositions of this invention unless otherwise indicated, provided that the utility of the composition as a whole is not eliminated by the presence of such other isomers. In particular, compounds of the invention contain a chiral center at the alkylene carbon in formulas (I)–(IV) to which the hydroxy group is attached.

When a mixture of stereoisomers is employed, it is advantageous for the amount of the (R) stereoisomer to be greater than the amount of the corresponding (S) stereoisomer. When comparing stereoisomers of the same compound, the (R) stereoisomer is preferred over the (S) stereoisomer.

General Synthetic Procedures

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be used to prevent certain functional groups from undergoing undesired reactions. The choice of a suitable protecting group for a particular functional group, as well as suitable conditions for protection and deprotection, are well known in the art. Representative examples of amino-protecting groups and hydroxy-protecting groups are given above. Typical procedures for their removal include the following. An acyl amino-protecting group or hydroxy-protecting group may conveniently be removed, for example, by treatment with an acid, such as trifluoroacetic acid. An arylmethyl group may conveniently be removed by hydrogenolysis over a suitable metal catalyst such as palladium on carbon. A silyl hydroxy-protecting group may conveniently be removed by treatment with a fluoride ion source, such as tetrabutylammonium fluoride, or by treatment with an acid, such as hydrochloric acid.

In addition, numerous protecting groups (including amino-protecting groups and hydroxy-protecting groups), and their introduction and removal, are described in Greene and Wuts, *Protecting Groups in Organic Synthesis,* 2nd Edition, John Wiley & Sons, NY, 1991, and in McOmie, *Protecting Groups in Organic Chemistry*, Plenum Press, NY, 1973.

Processes for preparing compounds of the invention are provided as further embodiments of the invention and are illustrated by the procedures below.

A compound of formula (I) can be prepared from a corresponding intermediate of formula (V):

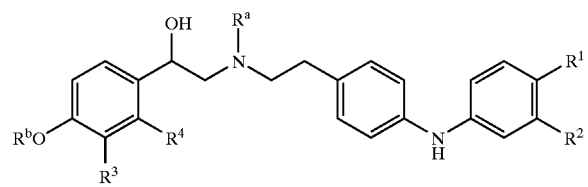

(V)

wherein $R^a$ is hydrogen and $R^b$ is a hydroxy-protecting group. Accordingly, the invention provides a method for preparing a compound of formula (I), comprising deprotecting a corresponding compound of formula (V), wherein $R^a$ is hydrogen, $R^b$ is a hydroxy-protecting group (e.g. benzyl,) and $R^1$–$R^4$ have any of the values defined above.

A compound of formula (I) can also be prepared by deprotecting a corresponding compound of formula (V) wherein $R^a$ is an amino-protecting group and wherein $R^b$ is a hydroxy-protecting group. Accordingly, the invention provides a method for preparing a compound of formula (I), comprising deprotecting a corresponding compound of formula (V) wherein $R^a$ is an amino-protecting group (e.g. 1,1-di-(4'-methoxyphenyl)methyl) or benzyl) and $R^b$ is a hydroxy-protecting group (e.g. benzyl).

An intermediate compound of formula (V) can be prepared by reacting an amine of formula (VI):

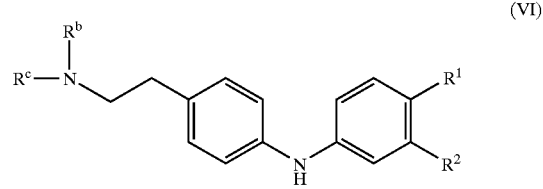

(VI)

wherein $R^a$ is hydrogen or an amino-protecting group (e.g. benzyl) and $R^c$ is hydrogen with a compound of formula (VII), (VIII), or (IX):

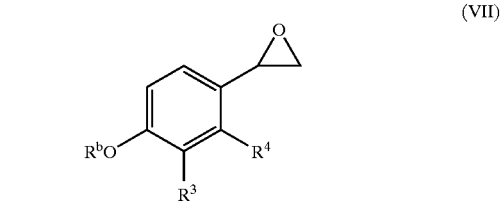

(VII)

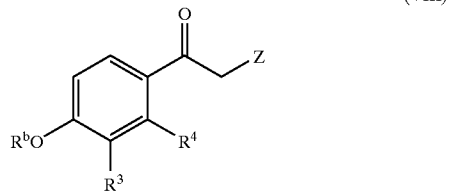

(VIII)

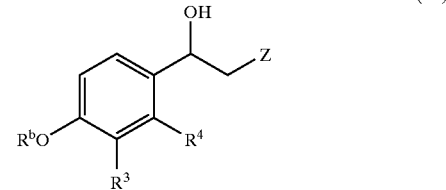

(IX)

wherein $R^b$ is a hydroxy-protecting group and Z is a suitable leaving group (e.g. bromo.)

Accordingly, the invention provides a method for preparing a compound of formula (V), comprising reacting a corresponding amine of formula (VI), wherein $R^a$ is hydrogen or an amino-protecting group and $R^c$ is hydrogen, with a corresponding compound of formula (VII), (VIII), or (IX) wherein $R^b$ is a hydroxy-protecting group and Z is a suitable leaving group (e.g. bromo). Suitable conditions for this reaction as well as suitable leaving groups are illustrated in the Examples and are also known in the art.

An intermediate compound of formula (V) can also be prepared by reacting a corresponding amine of formula (VI), wherein $R^a$ and $R^c$ are hydrogen, with a compound of formula (X):

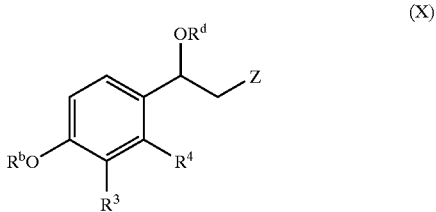

wherein $R^b$ is a hydroxy-protecting group (e.g. benzyl,) $R^d$ is a hydroxy-protecting group (e.g. tert-butyldimethylsilyl,) and Z is a leaving group, and subsequently removing the protecting group $R^d$.

Alternatively, an intermediate compound of formula (V), wherein $R^a$ is hydrogen is prepared by reacting a compound of formula (XI) with an aniline of formula (XII),

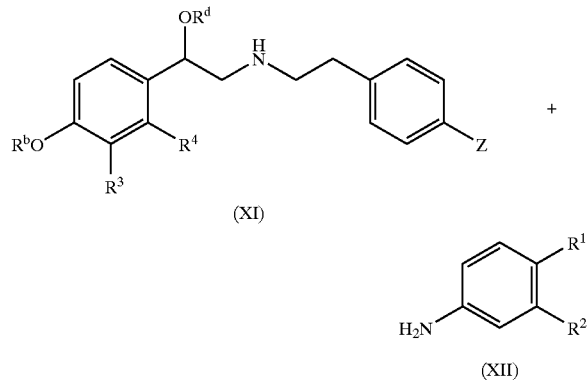

wherein $R^b$ is a hydroxy-protecting group (e.g. benzyl,) $R^d$ is a hydroxy-protecting group (e.g. tert-butyldimethylsilyl,) and Z is a leaving group, in the presence of a transition metal catalyst, and subsequently removing the protecting group $R^d$.

Additionally, a useful intermediate for preparing a compound of formula (VI), wherein $R^a$ is an amino-protecting group and $R^c$ is hydrogen, is a corresponding compound of formula (VI) wherein $R^a$ is an amino-protecting group and $R^c$ is an amino-protecting group that can be removed in the presence of $R^a$ (e.g. tert-butoxycarbonyl). Thus, the invention also provides novel intermediates of formula (VI), wherein $R^a$ is hydrogen or an amino-protecting group, $R^c$ is hydrogen or an amino-protecting group, and wherein $R^1$ and $R^2$ have any of the values defined herein. A preferred compound of formula (VI) is a compound wherein $R^a$ is an arylmethyl protecting group (e.g. benzyl) and $R^c$ is an alkoxycarbonyl protecting group (e.g. tert-butoxycarbonyl). Another preferred compound of formula (VI) is a compound wherein $R^a$ is hydrogen, and $R^c$ is an alkoxycarbonyl protecting group (e.g. tert-butoxycarbonyl).

The invention also provides a method for preparing a compound of formula (V) comprising reacting a corresponding compound of formula (VI) wherein $R^a$ and $R^b$ are each hydrogen with a corresponding compound of formula (X).

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as corn starch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intramuscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 $\mu$m. A typical formulation for use in a conventional nebulizer device is an isotonic aqueous solution of a pharmaceutical salt of the active agent at a concentration of the active agent of between about 0.05 $\mu$g/mL and about 10 mg/mL.

DPI's typically administer a therapeutic agent in the form of a free flowing powder that can be dispersed in a patient's air-stream during inspiration. In order to achieve a free flowing powder, the therapeutic agent can be formulated with a suitable excipient, such as lactose or starch. A dry powder formulation can be made, for example, by combining dry lactose having a particle size between about 1 $\mu$m and about 100 $\mu$m with micronized particles of a pharmaceutical salt of the active agent and dry blending. Alternative, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, NC) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239, 993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.01% to about 5% by weight of a pharmaceutical salt of active ingredient, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the pharmaceutical salt of active compound, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,277.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874, 063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compound is effective over a wide dosage range and is generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agent for inhalation administration are in the general range of from about 0.05 $\mu$g/day to about 1000 $\mu$g/day, preferably from about 0.5 $\mu$g/day to about 500 $\mu$g/day. A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 $\mu$g/day to about 100 mg/day, preferably about 0.5 $\mu$g/day to about 1000 $\mu$g/day.

The present active agents can also be co-administered with one or more other therapeutic agents. For example, for the treatment of asthma or of chronic obstructive pulmonary disease, the present agents can be administered in combination with a muscarinic receptor antagonist (e.g. ipatropium bromide or tiotropium) or a steroidal anti-inflammatory agent (e.g. fluticasone propionate, beclomethasone, budesonide, mometasone, ciclesonide, or triamcinolone). In addition, the present active agents can be co-administered with an agent having anti-inflammatory and/or bronchodilating or other beneficial activity, including but not limited to, a phosphodiesterase (PDE) inhibitor (e.g. theophylline); a PDE4 inhibitor (e.g. cilomilast or roflumilast); an immunoglobulin antibody (αIgE antibody); a leukotriene antagonist (e.g. monteleukast); a cytokine antagonist therapy, such as, an interleukin antibody (αIL antibody), specifically, an αIL-4 therapy, an αIL-13 therapy, or a combination thereof; a protease inhibitor, such as an elastase or tryptase inhibitor; cromolyn sodium; nedocromil sodium; and sodium cromoglycate. Further, the present agents can be co-administered with an antiinfective agent or antihistamines. Suitable doses for the other therapeutic agents administered in combination with a compound of the invention are in the range of about 0.05 µg/day to about 100 mg/day.

Accordingly, the compositions of the invention can optionally comprise a compound of the invention as well as another therapeutic agent as described above.

Additional suitable carriers for formulations of the active compounds of the present invention can be found in *Remington: The Science and Practice of Pharmacy*, 20th Edition, Lippincott Williams & Wilkins, Philadelphia, Pa., 2000. The following non-limiting examples illustrate representative pharmaceutical compositions of the invention.

FORMULATION EXAMPLE A

This example illustrates the preparation of a representative pharmaceutical composition for oral administration of a compound of this invention:

| Ingredients | Quantity per tablet, (mg) |
| --- | --- |
| Active Compound | 2 |
| Lactose, spray-dried | 148 |
| Magnesium stearate | 2 |

The above ingredients are mixed and introduced into a hard-shell gelatin capsule.

FORMULATION EXAMPLE B

This example illustrates the preparation of another representative pharmaceutical composition for oral administration of a compound of this invention:

| Ingredients | Quantity per tablet, (mg) |
| --- | --- |
| Active Compound | 4 |
| Cornstarch | 50 |
| Lactose | 145 |
| Magnesium stearate | 5 |

The above ingredients are mixed intimately and pressed into single scored tablets.

FORMULATION EXAMPLE C

This example illustrates the preparation of a representative pharmaceutical composition for oral administration of a compound of this invention.

An oral suspension is prepared having the following composition.

| Ingredients | |
| --- | --- |
| Active Compound | 0.1 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

FORMULATION EXAMPLE D

This example illustrates the preparation of a representative pharmaceutical composition containing a compound of this invention.

An injectable preparation buffered to a pH of 4 is prepared having the following composition:

| Ingredients | |
| --- | --- |
| Active Compound | 0.2 g |
| Sodium Acetate Buffer Solution (0.4 M) | 2.0 mL |
| HCl (1N) | q.s. to pH 4 |
| Water (distilled, sterile) | q.s. to 20 mL |

FORMULATION EXAMPLE E

This example illustrates the preparation of a representative pharmaceutical composition for injection of a compound of this invention.

A reconstituted solution is prepared by adding 20 mL of sterile water to 1 g of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

FORMULATION EXAMPLE F

This example illustrates the preparation of a representative pharmaceutical composition containing a compound of this invention.

An injectable preparation is prepared having the following composition:

| Ingredients | |
| --- | --- |
| Active Compound | 0.1–5.0 g |
| Hydroxypropyl-β-cyclodextrin | 1–25 g |
| 5% Aqueous Dextrose Solution (sterile) | q.s. to 100 mL |

The above ingredients are blended and the pH is adjusted to 3.5±0.5 using 0.5 N HCl or 0.5 N NaOH.

Formulation Example G

This example illustrates the preparation of a representative pharmaceutical composition for topical application of a compound of this invention.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

FORMULATION EXAMPLE H

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

FORMULATION EXAMPLE I

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
| --- | --- |
| Pharmaceutical salt of active compound | 0.2 |
| Lactose | 25 |

The pharmaceutical salt of active compound is micronized prior to blending with lactose. The contents of the cartridges are administered using a powder inhaler.

FORMULATION EXAMPLE J

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 µg and about 100 µg of active drug ingredient per dose.

FORMULATION EXAMPLE K

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

FORMULATION EXAMPLE L

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into canisters with pressurized 1,1,1,2, 3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using in vitro Tests A–C below, in vivo Test D, below, or can be demonstrated using other tests that are known in the art.

| Abbreviations | |
| --- | --- |
| % Eff | % efficacy |
| ATCC | American Type Culture Collection |
| BSA | Bovine Serum Albumin |
| cAMP | Adenosine 3':5'-cyclic monophosphate |
| DMEM | Dulbecco's Modified Eagle's Medium |
| DMSO | Dimethyl sulfoxide |
| EDTA | Ethylenediaminetetraacetic acid |
| Emax | maximal efficacy |
| FBS | Fetal bovine serum |
| Gly | Glycine |
| HEK-293 | Human embryonic kidney - 293 |
| PBS | Phosphate buffered saline |
| rpm | rotations per minute |
| Tris | Tris(hydroxymethyl)aminomethane |

Membrane Preparation from Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 µg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @ 4° C., one tablet of "Complete Protease Inhibitor Cocktail Tablets with 2 mM EDTA" per 50 mL buffer (Roche cat.# 1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM $MgCl_2$, 1 mM EDTA @ 25° C.). Protein concentration of the membrane suspension was determined by the method of Bradford (Bradford M M., *Analytical Biochemistry*, 1976, 72, 248–54). Membranes were stored frozen in aliquots at −80° C.

Test A

Radioligand Binding Assay on Human $\beta_1$ and $\beta_2$ Adrenergic Receptors

Binding assays were performed in 96-well microtiter plates in a total assay volume of 100 μL with 5 μg membrane protein for membranes containing the human $\beta_2$ adrenergic receptor, or 2.5 μg membrane protein for membranes containing the human $\beta_1$ adrenergic receptor in assay buffer (75 mM Tris/HCl pH 7.4 @ 25° C., 12.5 mM $MgCl_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM–200 nM. Displacement assays for determination of $pK_i$ values of compounds were done with [$^3$H]dihydroalprenolol at 1 nM and 10 different concentrations of compound ranging from 40 pM–10 μM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 μM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @ 4° C., 12.5 mM $MgCl_2$, 1 mM EDTA) to remove unbound radioactivity. Plates were dried, 50 μL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM alprenolol. $K_i$ values for compounds were calculated from observed $IC_{50}$ values and the $K_d$ value of the radioligand using the Cheng-Prusoff equation (Cheng Y, and Prusoff W H., *Biochemical Pharmacology*, 1973, 22, 23, 3099–108). The receptor subtype selectivity was calculated as the ratio of $K_i(\beta_1)/K_i(\beta_2)$. All of the compounds tested demonstrated a selectivity greater than about 20.

Test B

Whole-Cell cAMP Flashplate Assay with a Cell Line Heterologously Expressing Human $\beta_2$ Adrenergic Receptor For the determination of agonist potencies, a HEK-293 cell line stably expressing cloned human $\beta_2$ adrenergic receptor (clone H24.14) was grown to confluency in medium consisting of DMEM supplemented with 10% FBS and 500 μg/mL Geneticin. The day before the assay, antibiotics were removed from the growth-medium.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. at a final concentration of 800,000 cells/mL. Cells were used at a final concentration of 40,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA). Compounds were tested in the assay at 10 different concentrations, ranging from 2.5 μM to 9.5 pM. Reactions were incubated for 10 min at 37° C. and stopped by addition of 100 μl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. Agonist potencies were expressed as $pEC_{50}$ values. All of the compounds tested demonstrated $pEC_{50}$ values greater than about 7.

Test C

Whole-Cell cAMP Flashplate Assay with a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701–11). Cells were grown to 75–90% confluency in complete, serum-free medium (LHC-9 MEDIUM containing Epinephrine and Retinoic Acid, cat # 181-500, Biosource International, Camarillo, Calif.). The day before the assay, medium was switched to LHC-8 (No epinephrine or retinoic acid, cat # 141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer (75 mM Tris/HCl pH 7.4 @ 25° C., 12.5 mM $MgCl_2$, 1 mM EDTA, 0.2% BSA).

Compounds were tested in the assay at 10 different concentrations, ranging from 10 $\mu$M to 40 pM. Maximal response was determined in the presence of 10 $\mu$M Isoproterenol. Reactions were incubated for 10 min at 37° C. and stopped by addition of 100 $\mu$l ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for samples and cAMP standards, as described in the manufacturer's user manual. Data were analyzed by nonlinear regression analysis with the GraphPad Prism Software package (GraphPad Software, Inc., San Diego, Calif.) using the 4-parameter model for sigmoidal dose-response with variable slope. All of the compounds tested demonstrated $pEC_{50}$ values greater than about 7.

Compound efficacy (% Eff) was calculated from the ratio of the observed maximum of the fitted curve and the maximal response obtained for 10 $\mu$M isoproterenol and was expressed as % Eff relative to isoproterenol. The compounds tested demonstrated a % Eff greater than about 20.

Test D

Assay of Bronchoprotection Against Acetylcholine-Induced Bronchospasm in a Guinea Pig Model Groups of 6 male guinea pigs (Duncan-Hartley (HsdPoc:DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Following a 60 minute acclimation period and a 10 minute exposure to nebulized water for injection (WFI), guinea pigs were exposed to an aerosol of test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre-and post-nebulization weights of the filled nebulizer.

The bronchoprotective effects of compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2–5 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of a 0.1 mg/mL solution of acetylcholine (Ach), (Sigma-Aldrich, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic cocktail. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways had not collapsed and that the animal did not suffer from hyperventilation.

Once it was determined that baseline values were within the range 0.3–0.9 mL/cm $H_2O$ for compliance and within the range 0.1–0.199 cm $H_2O$/mL per second for resistance, the pulmonary evaluation was initiated. A Buxco pulmonary measurement computer progam enabled the collection and derivation of pulmonary values. Starting this program initiated the experimental protocol and data collection. The changes in volume over time that occured within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach was infused intravenously for 1 minute from a syringe pump (sp210iw, World Precision Instruments, Inc., Sarasota, Fla.) at the following doses and prescribed times from the start of the experiment: 1.9 $\mu$g/minute at 5 minutes, 3.8 $\mu$g/minute at 10 minutes, 7.5 $\mu$g/minute at 15 minutes, 15.0 $\mu$g/minute at 20 minutes, 30 $\mu$g/minute at 25 minutes and 60 $\mu$g/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second) (Giles et al., 1971). Once the pulmonary function measurements were completed at minute 35 of this protocol, the guinea pig was removed from the plethysmograph and euthanized by $CO_2$ asphyxiation.

The quantity $PD_2$, which is defined as the amount of Ach needed to cause a doubling of the baseline pulmonary resistance, was calculated using the pulmonary resistance values derived from the flow and the pressure over a range of Ach challenges using the following equation. This was derived from the equation used to calculate $PC_{20}$ values in the clinic (Am. Thoracic Soc, 2000).

$$PD_2 = \text{antilog}\left[\log C_1 + \frac{(\log C_2 - \log C_1)(2R_0 - R_1)}{R_2 - R_1}\right]$$

where:

$C_1$=Second to last Ach concentration (concentration preceding $C_2$)

$C_2$=Final concentration of Ach (concentration resulting in a 2-fold increase in pulmonary resistance ($R_L$))

$R_0$=Baseline $R_L$ value $R_1$=$R_L$ value after $C_1$ $R_2$=$R_L$ value after $C_2$ Statistical analysis of the data was performed using a One-Way Analysis of Variance followed by post-hoc analysis using a Bonferroni/Dunn test. A P-value <0.05 was considered significant.

Dose-response curves were fitted with a four parameter logistic equation using GraphPad Prism, version 3.00 for Windows (GraphPad Software, San Diego, Calif.)

$Y=\text{Min}+(\text{Max}-\text{Min})/(1+10\hat{\,}((\log ED_{50}-X)*\text{Hillslope}))$, where X is the logarithm of dose, Y is the response ($PD_2$), and Y starts at Min and approaches asymptotically to Max with a sigmoidal shape.

Representative compounds of the invention were found to have significant bronchoprotective activity at time points beyond 24 hours post-dose.

The following synthetic examples are offered to illustrate the invention, and are not to be construed in any way as limiting the scope of the invention.

EXAMPLES

In the examples below, the following abbreviations have the following meanings. Any abbreviations not defined have their generally accepted meaning. Unless otherwise stated, all temperatures are in degrees Celsius.

| | |
|---|---|
| Bn = | benzyl |
| DMSO = | dimethyl sulfoxide |
| EtOAc = | ethyl acetate |
| TFA = | trifluoroacetic acid |
| THF = | tetrahydrofuran |
| MgSO$_4$ = | anhydrous magnesium sulfate |
| NaHMDS = | sodium hexamethyldisilazane |
| TMSCl = | trimethylsilyl chloride |
| DMF = | dimethyl formamide |
| Boc = | tert-butoxycarbonyl |
| TBS = | tert-butyldimethylsilyl |

General: Unless noted otherwise, reagents, starting material and solvents were purchased from commercial suppliers, for example Sigma-Aldrich (St. Louis, Mo.), J. T. Baker (Phillipsburg, N.J.), Honeywell Burdick and Jackson (Muskegon, Mich.), and Trans World Chemicals, Inc. (TCI) (Rockville, Md.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC as described below; NMR samples were dissolved in deuterated solvent (CD$_3$OD, CDCl$_3$, or DMSO-d6), and spectra were acquired with a Varian Gemini 2000 instrument (300 MHz) using the residual protons of the listed solvent as the internal standard unless otherwise indicated; and mass spectrometric identification was performed by an electrospray ionization method (ESMS) with a Perkin Elmer instrument (PE SCIEX API 150 EX).

Example 1

Synthesis of N-{2-[4-(3-phenyl-4-methoxyphenyl) aminophenyl]ethyl}-2-hydroxy-2-(3-hydroxymethyl-4-hydroxyphenyl)ethylamine (1)

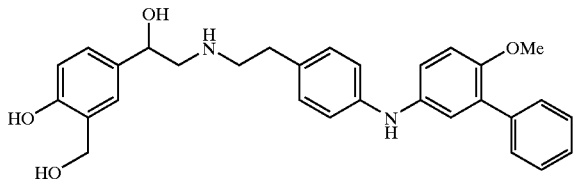

To 62 mg (0.1 mmol) of compound bb from part e below and 0.1 mmol of 4-methoxy-3-phenylaniline hydrochloride in 0.15 mL of toluene were added 9.3 mg (0.015 mmol) of racemic bis(diphenylphosphino)-1,1'-binaphthyl (Aldrich) in 0.15 mL toluene, 4.6 mg (0.05 mmol) of tris (dibenzylidineacetone)dipalladium(0) (Aldrich) in 0.1 mL toluene, and 29 mg (0.3 mmol) of sodium tert-butoxide slurried in 0.4 mL toluene. The mixture was shaken and heated at 80° C. for 5 hours. Acetic acid (80% aq., 0.6 mL) was added and the mixture was shaken and heated at 80° C. for 5 hours. The resulting material was diluted to 2 mL total volume with DMF, filtered, and purified by reversed phase HPLC, using acetonitrile in aqueous TFA, and using a mass-triggered, automated collection device. The product-containing fractions were analyzed by analytical LC-MS, and freeze-dried to give a TFA salt of compound 1 as a powder. n/z: [M+H$^+$] calcd for C$_{30}$H$_{32}$N$_2$O$_4$ 485.24. found 485.2.

The intermediate compound bb was prepared as follows.

a. Synthesis of Compound xx.

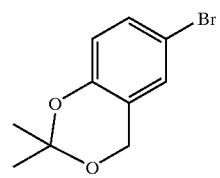

To 5-bromo-2-hydroxybenzyl alcohol (93 g, 0.46 mol, available from Sigma-Aldrich) in 2.0 L of 2,2-dimethoxypropane was added 700 mL of acetone, followed by 170 g of ZnCl$_2$. After stirring for 18 hours, 1.0 M aqueous NaOH was added until the aqueous phase was basic. 1.5 L of diethyl ether was added to the slurry, and the organic phase was decanted into a separatory funnel. The organic phase was washed with brine, dried over Na$_2$SO$_4$, filtered, and concentrated under reduced pressure to give compound xx as a light orange oil.

b. Synthesis of Compound yy.

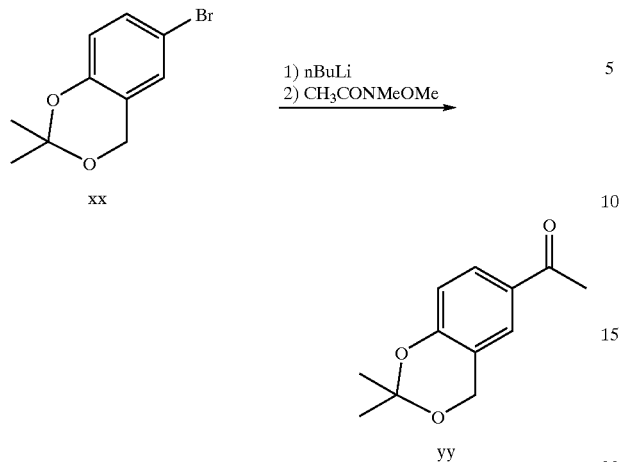

To 110 g (0.46 mol) of compound xx in 1.0 L of THF at −78° C. was added 236 mL (0.51 mol) of 2.14 M n-butyllithium in hexanes via a dropping funnel. After 30 minutes, 71 g (0.69 mol) of N-methyl-N-methoxyacetainide (available from TCI) was added. After 2 hours, the reaction was quenched with water, diluted with 2.0 L of 1.0 M aqueous phosphate buffer (pH=7.0), and extracted once with diethyl ether. The diethyl ether phase was washed once with brine, dried over $Na_2SO_4$, filtered, and concentrated under reduced pressure to give a light orange oil. The oil was dissolved in a minumum volune of ethyl acetate, diluted with hexanes, and the product crystallized to give compound yy as a white solid.

c. Synthesis of Compound zz.

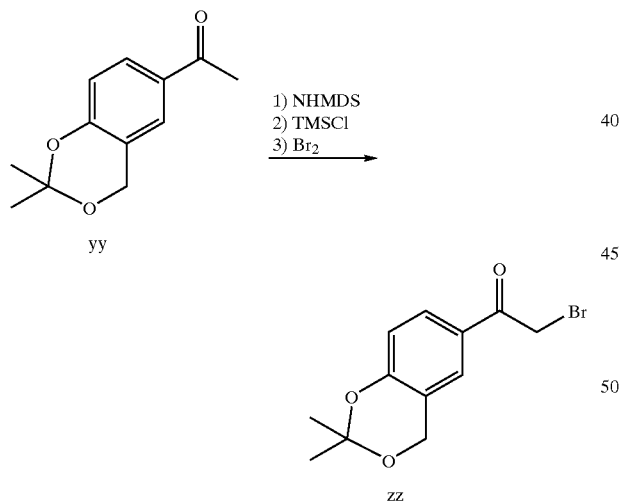

To 23.4 g (0.113 mol) of compound yy in 600 mL of THF at −78° C. was added 135 mL of 1.0 M NaHMDS in THF (Sigma-Aldrich). After 1 hour, 15.8 mL (0.124 mol) of TMSCl was added. After another 30 minutes, 5.82 mL (0.113 mol) of bromine was added. After a final 10 minutes, the reaction was quenched by diluting with diethyl ether and pouring onto 500 mL of 5% aqueous $Na_2SO_3$ premixed with 500 mL of 5% aqueous $NaHCO_3$. The phases were separated, and the organic phase was washed with brine, dried over $Na_2SO_4$, filtered, and concentrated under reduced pressure to give compound zz as a light orange oil that solidified in the freezer.

d. Synthesis of Compound aa.

Compound zz ⟶

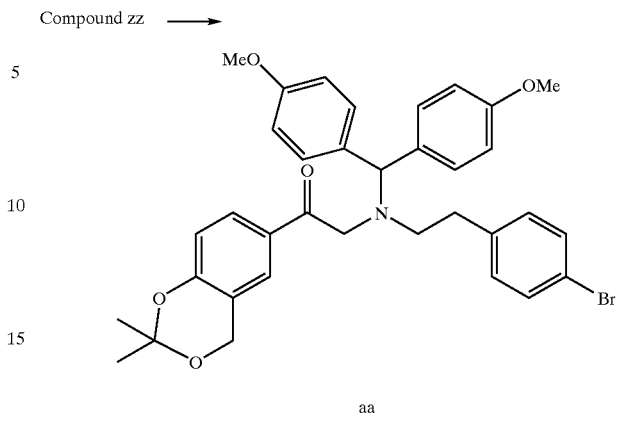

To 32 g (0.113 mol) of compound zz in 300 mL methylene chloride at 0° C. was added 31.6 mL (0.23 mol) of triethylamine, followed by 16.0 mL (0.10 mol) of 4-bromophenethylamine (Sigma-Aldrich). After 2 hours, 27 g (0.10 mol) of di-(4-methoxyphenyl)chloromethane was added. After 30 minutes, the slurry was partitioned between 50% saturated aqueous $NaHCO_3$ and diethyl ether, and the phases were separated. The organic phase was washed once each with water and brine, dried over $K_2CO_3$, filtered, and concentrated to an orange oil. The oil was purified by chromatography (1400 mL silica gel, eluted with 3 acetonitrile/0.5 triethylamine/96.5 methylene chloride) to give compound aa as a light orange foam.

e. Synthesis of Compound bb.

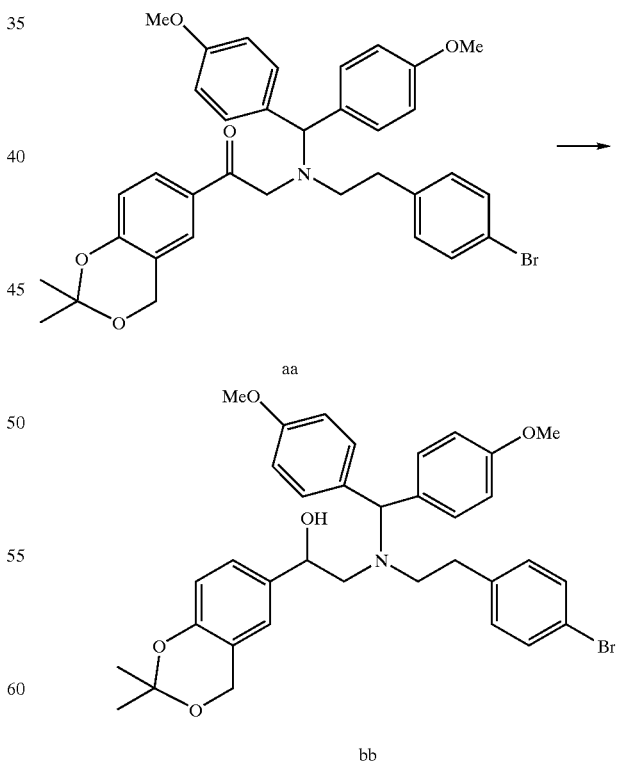

To 41 g (65 mmol) of compound aa in 120 mL of THF was added 200 mL of methanol, followed by 2.46 g (65 mmol) of sodium borohydride. After 1 hour, the solution was partitioned between 1.0 M aqueous phosphate buffer (pH 7.0) and diethyl ether, and the phases were separated. The diethyl ether phase was washed with brine, dried over $K_2CO_3$, filtered, and concentrated to an oil. The oil was purified by chromatography (1200 mL silica gel, eluted with 18 acetone/0.5 triethylamine/81.5 hexanes) to give compound bb as a white foam.

Example 2

Synthesis of N-{2-[4-(4-ethoxyphenyl)aminophenyl]ethyl}-2-hydroxy-2-(3-hydroxymethyl-4-hydroxyphenyl)ethylamine (2)

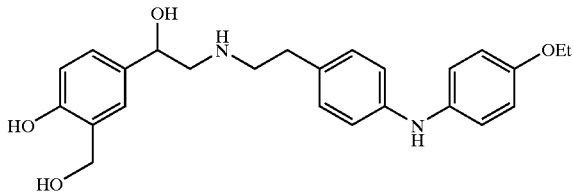

Using a coupling procedure similar to that described in Example 1, except replacing the 4-methoxy-3-phenylaniline hydrochloride with 4-ethoxyaniline, a TFA salt of compound 2 was prepared.

Example 3

Synthesis of N-{2-[4-(3-phenylphenyl)aminophenyl]ethyl}-2-hydroxy-2-(3-hydroxymethyl-4-hydroxyphenyl)ethylamine (3)

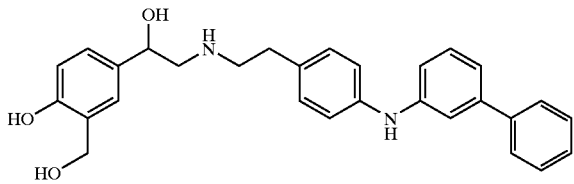

Using a coupling procedure similar to that described in Example 1, except replacing the 4-methoxy-3-phenylaniline hydrochloride with 3-phenylaniline, a TFA salt of compound 3 was prepared.

Example 4

Synthesis of N-{2-[4-(4-ethoxyphenyl)aminophenyl]ethyl}-(R)-2-hydroxy-2-(3-hydroxymethyl-4-hydroxyphenyl)ethylamine (4)

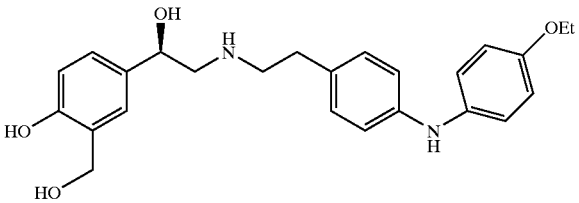

To a mixture of 3.0 g (4.98 mmol) of compound F, prepared in part e below, in 70 mL of ethanol was added 1.0 g of 10% palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 40 mL of 1:1 isopropanol: methanol, 2.74 mL of 4.0 N HCl in dioxane was added, and the product was precipitated as the di-HCl salt by adding the solution to a large volume of EtOAc. The solids were isolated by filtration to give the di-HCl salt of compound 4 as a white solid. $^1$H NMR (300 MHz, DMSO-d6) δ 8.94 (br s, 1H), 8.63 (br s, 1H), 6.97–6.67 (m, 11H), 4.76 (m, 1H), 4.39 (s, 2H), 4.29 (br, 4H), 3.87 (dd, 2H), 3.02–2.76 (m, 6H), 1.22 (t, 3H); m/z: [M+H$^+$] calcd for $C_{25}H_{30}N_2O_4$ 423.23. found 423.2.

The intermediate compound F was prepared as follows.
a. Synthesis of Compound A.

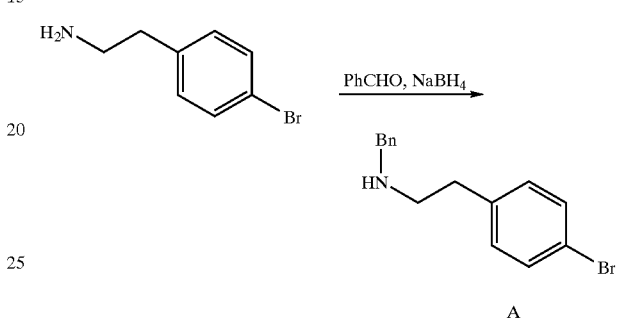

To 10.7 g (53.0 mmol) of 4-bromophenethylamine (available from Sigma-Aldrich) in 100 mL of toluene was added 6.80 g (64 mmol) of benzaldehyde. After stirring for 10 minutes, the cloudy mixture was concentrated under reduced pressure. The residue was re-concentrated twice from toluene, and the clear oil was dissolved in 50 mL of tetrahydrofuran. 2.0 g (53 mmol) of sodium borohydride was added to the solution, followed by 20 mL of methanol, and the flask was stirred in a water bath at ambient temperature for one hour. 1.0 N aqueous HCl was added until the pH was below 1. The slurry was stirred in an ice bath for 30 minutes, and the solids were isolated by filtration, rinsed with cold water, and air dried to give the hydrochloride salt of compound A as a colorless solid. $^1$H NMR (300 MHz, DMSO-d6) δ 9.40 (s, 2H), 7.50–7.32 (m, 7H), 7.14 (d, 2H), 4.07 (s, 2H), 3.03 (m, 2H), 2.92 (m, 2H).
b. Synthesis of Compound B.

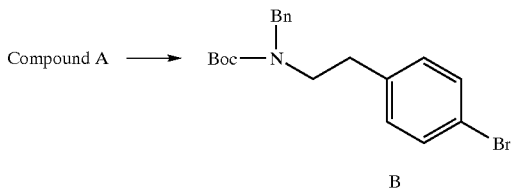

To 5.0 g (15 mmol) of compound A in 100 mL of methanol was added 1.70 g (16.5 mmol) of triethylamine. The solution was cooled in an ice/water bath, and 3.66 g (16.8 mmol) of di-tert-butyldicarbonate was added. After 3.5 hours, the solution was concentrated under reduced pressure, and the residue was partitioned between 1.0 M aqueous $NaHSO_4$ and diethyl ether, and the phases were separated. The diethyl ether phase was washed with water followed by brine, dried over $Na_2SO_4$, filtered, and concentrated to give compound B (6.1 g, 93%) as a colorless oil. $^1$H NMR (300 MHz, DMSO-d6) δ 7.38 (d, 2H), 7.28–7.13 (m, 5H), 7.04 (m, 2H), 4.29 (br s, 2H), 3.20 (m, 2H), 2.62 (m, 2H), 1.25 (s, 9H).

c. Synthesis of Compound C.

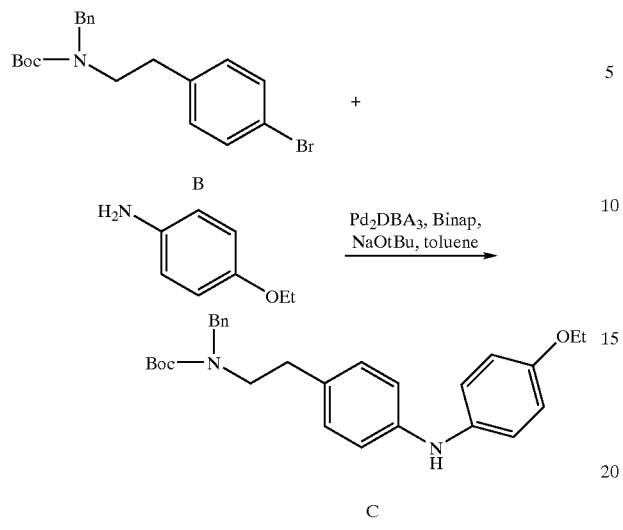

To a flask containing 3.0 g (7.7 mmol) of compound B, 1.26 g (9.1 mmol) of para-phenetidine (4-ethoxyaniline, available from Sigma-Aldrich), 0.32 g (0.35 mmol) of tris(dibenzylidineacetone)dipalladium(0), 0.65 g (1.05 mmol) of rac-2,2'-bis(diphenylphosphino)-1,1'-binaphthyl, and 0.88 g (9.1 mmol) of sodium tert-butoxide was added 35 mL of toluene, and the mixture was heated at 95° C. for 5.5 hours under a nitrogen atmosphere. The mixture was partitioned between 1.0 M aqueous $NaHSO_4$ and diethyl ether, and the phases were separated. The diethyl ether phase was diluted with one volume of hexanes, and was washed once each with 1.0 M aqueous $NaHSO_4$ and brine, dried over $Na_2SO_4$, filtered, and concentrated to a dark oil. The oil was purified by chromatography, using 15% EtOAc/85% hexanes as eluent, to give 2.52 g (73%) of compound C as a dark orange oil. $^1$H NMR (300 MHz, DMSO-d6) δ 7.64 (s, 1H), 7.28–7.13 (m,5H), 6.91–6.72 (m, 8H), 4.27 (s, 2H), 3.92 (q, 2H), 3.25 (s, 2H), 3.15 (m, 2H), 2.52 (m, 2H), 1.31 (s, 9H), 1.21 (t, 3H). m/z: [M+H$^+$] calcd for $C_{28}H_{34}N_2O_3$ 447.3. found 447.8.

d. Synthesis of Compound E.

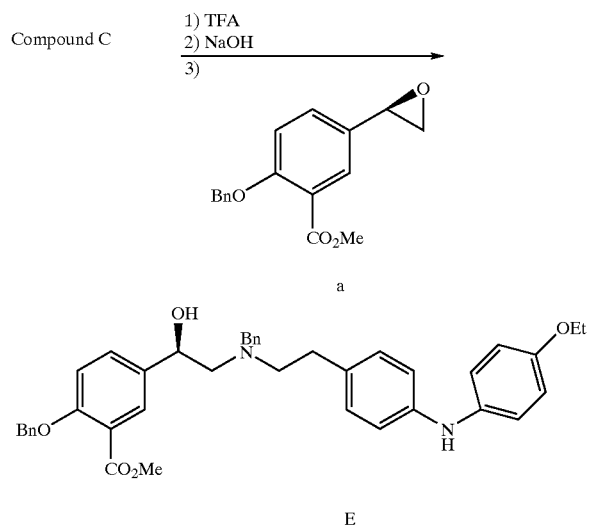

To 2.93 g (6.56 mmol) of compound C in 15 mL of $CH_2Cl_2$ at 0° C. was added 15 mL of trifluoroacetic acid. After 40 minutes, the solution was concentrated under reduced pressure, and the residue was partitioned between 1.0 M aqueous NaOH and EtOAc. The phases were separated, and the EtOAc phase was washed once each with water and brine, dried over $Na_2SO_4$, filtered, and concentrated to an orange oil. The oil was dissolved in 20 mL of isopropanol, 1.86 g (6.56 nmuol) of epoxide a was added, and the solution was heated at 78° C. overnight. The mixture was cooled to room temperature, and concentrated under reduced pressure to give compound E as an orange oil that was used without purification in the next step.

e. Synthesis of Compound F.

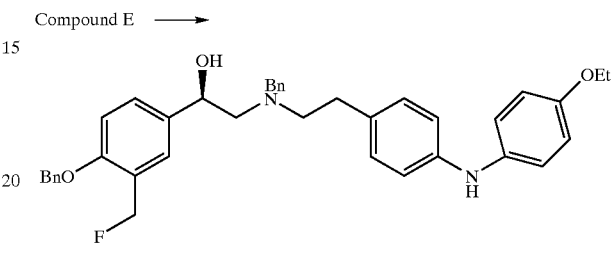

To 6.56 mmol of crude compound E from the previous step in 40 mL of tetrahydrofuran at 0° C. was added 16.4 mL (16.4 mmol) of 1.0 M lithium aluminum hydride in tetrahydrofuran. After 2 hours, the reaction was quenched by slow addition of sodium sulfate decahydrate. The slurry was diluted with diethyl ether, dried over $Na_2SO_4$, filtered, and concentrated to an orange oil. The oil was purified by silica gel chromatography, using 50% EtOAc/50% hexanes as eluent, to give 3.0 g (76%, 2 steps) of compound F as an off-white foam. $^1$H NMR (300 MHz, DMSO-d6) δ 7.61 (s, 1H), 7.37–6.71 (m, 21H), 5.02 (s, 2H), 4.94 (m, 1H), 4.67 (m, 1H), 4.55 (m, 1H), 4.48 (d, 2H), 3.85 (dd, 2H), 3.63 (dd, 2H), 2.53 (m, 6H), 1.21 (t, 3H).

The intermediate epoxide a can be prepared as described by R. Hett et al., *Tetrahedron Lett.*, 1994, 35, 9357–9378.

Example 5

Synthesis of N-{2-[4-(4-ethoxyphenyl)aminophenyl]ethyl}-(R)-2-hydroxy-2-(3-formamido-4-hydroxyphenyl)ethylamine (5)

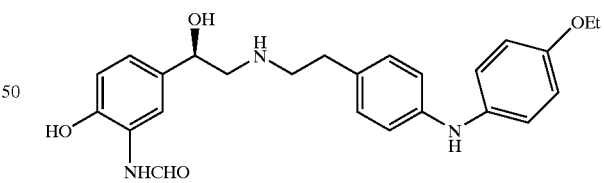

To a mixture of 580 mg (0.93 mmol) of compound V in 25 mL of ethanol was added 173 mg of 10% palladium on carbon under a stream of nitrogen. The flask was fitted with a balloon of hydrogen gas, and the reaction was vigorously stirred for 4 days. The reaction was filtered and the filtrate was concentrated under reduced pressure. The residue was purified by reverse phase HPLC using a gradient of 10 to 50% acetonitrile in 0.1% aqueous TFA. Fractions containing pure product were combined and lyophilized to afford a TFA salt of compound 5 as an off-white powder.

A sample of the TFA salt of compound 5 (150 mg) was dissolved in acetonitrile (2.0 mL) and water (2.0 mL). 0.1N HCl (7.0 mL, 0.70 mmol) was added, and the resulting precipitate was redissolved by the addition of acetonitrile. The resulting solution was lyophilized to give a solid which was again dissolved in acetonitrile (5.0 mL) and water (5.0 mL). 0.1N HCl (7.0 mL, 0.70 mmol) was added and the resulting solution was lyophilized to give a hydrochloride salt of compound 5 as an off white powder. $^1$H NMR (300 MHz, DMSO-d6) δ 10.10 (br s, 1H), 9.62 (s, 1H), 8.80 (br s, 1H), 8.65 (br s, 1H), 8.27 (d, 1H), 8.15 (d, 1H), 6.80–7.15 (m, 11H), 4.78 (dd, 1H), 3.94 (quar, 2H), 2.80–3.15 (m, 6H), 1.29 (t, 3H); m/z: [M+H$^+$] calcd for $C_{25}H_{29}N_3O_4$ 436.22; found 436.3.

The intermediate compound V was prepared as follows.

a. Synthesis of Compound V.

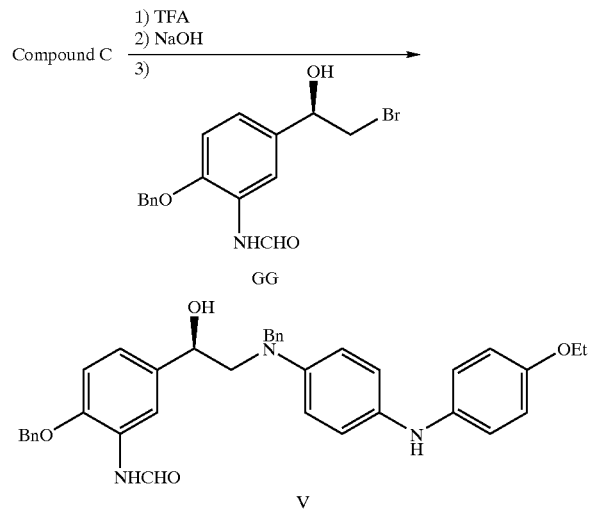

To 0.60 g (1.3 mmol) of compound C (from Example 4, part c) in 20 mL of CH$_2$Cl$_2$ at 0° C. was added 2.0 mL of trifluoroacetic acid. After 1 h, the solution was concentrated under reduced pressure, and the residue was partitioned between 1.0 M aqueous NaOH and EtOAc. The phases were separated, and the EtOAc phase was dried over MgSO$_4$, filtered, and concentrated to an oil and dissolved in 10 mL of 1:1 methanol:THF. Bromohydrin GG (360 mg, 1.0 mmol) and K$_2$CO$_3$ (380 mg, 2.7 mmol) were added and the reaction was stirred at room temperature for 1.5 h. The reaction was diluted with 30 mL water and extracted twice with 30 mL portions of toluene. The toluene extracts were combined, dried over MgSO$_4$, filtered, and concentrated. The residue was heated to 120° C. After 2 h, the residue was cooled to room temperature and purified by silica gel chromatography (gradient of 5 to 10% methanol in CH$_2$Cl$_2$). Fractions containing pure product were combined and concentrated to afford compound V as a tan solid.

The intermediate bromohydrin GG can be prepared as described in U.S. Pat. No. 6,268,533 B 1; and in R. Hett et al., *Organic Process Research and Development*, 1998, 2, 96–99. The intermediate bromohydrin GG can also be prepared using procedures similar to those described by Hong et al., *Tetrahedron Lett.*, 1994, 35, 6631; or similar to those described in U.S. Pat. No. 5,495,054.

Example 6

Synthesis of N-{2-[4-(4-ethoxyphenyl) aminophenyl]ethyl}-(R)-2-hydroxy-2-(8-hydroxy-2 (1H)-quinolinon-5-yl)ethylamine (6)

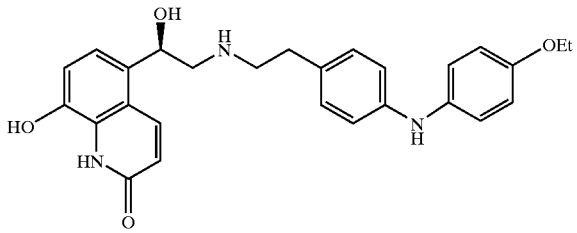

To a solution of 200 mg of compound Q (0.36 mmol) in 5.0 mL methanol was added 45 mg of 10% palladium on carbon. The reaction was placed under 1 atm H$_2$ gas. After 20 h, an additional 25 mg of 10% palladium on carbon was added and the reaction was stirred under 1 atm H$_2$ for an additional 24 h after which time the reaction was filtered. The filtrate was concentrated and purified by reversed phase preparative HPLC (gradient of 15–50% acetonitrile in 0.1% TFA). Fractions containing pure product were combined and lyophilized to afford a TFA salt of compound 6 as a powder. A sample of the TFA salt (39.7 mg) was dissolved in acetonitrile (1.0 mL), diluted with water (2.0 mL) and then 0.1 N HCl (5.0 mL). The solution was frozen and lyophilized to afford the hydrochloride salt of compound 6 (38.3 mg) as a yellow powder. $^1$H NMR (300 MHz, DMSO-d6) δ 10.5 (br s, 2H), 9.20 (br s, 1H), 8.75 (br s, 1H), 8.22 (d, 1H) 7.15 (d, 1H), 6.95–7.05 (m, 5H), 6.80–6.90 (m, 4H), 6.56 (d, 1H), 5.40 (dd, 1H), 3.95 (quar, 2H), 2.95–3.18 (m, 4H), 2.80–2.95 (m, 2H), 1.29 (t, 3H); m/z: [M+H$^+$] calcd for $C_{27}H_{29}N_3O_4$ 460.22. found 460.2.

The intermediate compound Q was prepared as follows.

a. Synthesis of Compound X.

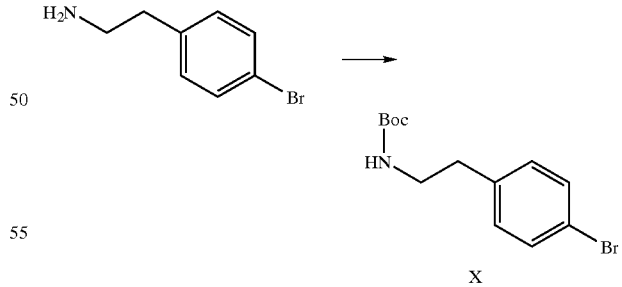

To 7.03 g (35.1 mmol) of 4-bromophenethylamine (Sigma-Aldrich) in 60 mL of THF was added 8.6 g (39.4 mmol) of di-tert-butyldicarbonate. After 10 minutes, the solution was concentrated under reduced pressure, and the residue was partitioned between saturated aqueous sodium bicarbonate and ethyl acetate. The ethyl acetate phase was washed with brine, dried over MgSO$_4$, filtered, and concentrated to give compound X as a white solid.

b. Synthesis of Compound Y.

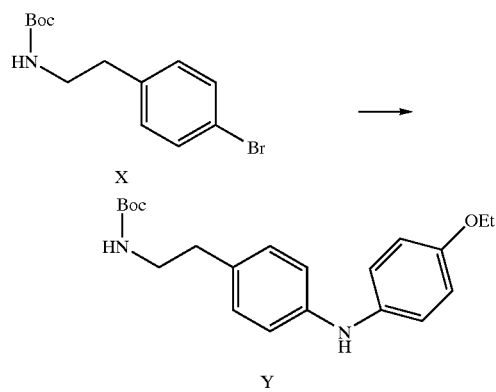

To a flask containing 1.2 g (4.1 mmol) of compound X, 0.72g (5.3 mmol) of para-phenetidine (4-ethoxyaniline, Sigma-Aldrich), 0.19 g (0.35 mmol) of tris(dibenzylidineacetone)dipalladium(0), 0.38 g (0.61 mmol) of rac-2,2'-bis(diphenylphosphino)-1,1'-binaphthyl, and 0.51 g (5.3 mmol) of sodium tert-butoxide, was added 35 mL of toluene, and the mixture was heated at 95° C. for 16 hours under an nitrogen atmosphere. The mixture was partitioned between 1.0 M aqueous NaHSO$_4$ and diethyl ether. The diethyl ether phase was washed once each with saturated NaHCO$_3$ and brine, dried over MgSO$_4$, filtered, and concentrated to a dark oil. The oil was purified by silica gel chromatography, using 15% EtOAc/85% hexanes as eluant, to give compound Y as a dark orange oil.

c. Synthesis of Compound Q.

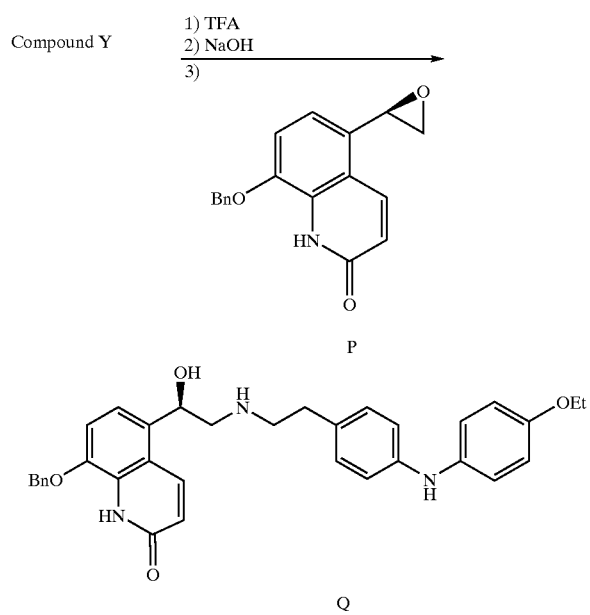

To 1.0 g of compound Y (2.8 mmol) in 5 mL CH$_2$Cl$_2$ was added 4 mL TFA. After 15 minutes, the solution was concentrated, diluted with 50 mL isopropyl acetate and washed twice with 1.0 M aqueous NaOH. The isopropyl acetate layer was dried over MgSO$_4$, filtered, and concentrated to a brown oil. The oil was dissolved in 5.0 mL of isopropanol and 390 mg (1.3 mmol) of epoxide P were added. The solution was heated to 70° C. After 36 h, the solution was concentrated and the product purified by reversed phase HPLC (gradient of 20–70% acetonitrile in 0.1% TFA). Fractions containing pure product were combined and concentrated to remove acetonitrile. The aqueous residue was diluted with brine and extracted with ethyl acetate. The ethyl acetate layer was dried over MgSO$_4$ and concentrated to afford compound Q as a yellow foam.

The intermediate epoxide P can be prepared as described in International Patent Application Publication Number WO 95/25104; and as described in EP 0 147 719 B.

Example 7
Synthesis of N-{2-[4-(3-phenyl-4-methoxyphenyl)aminophenyl]ethyl}-(R)-2-hydroxy-2-(3-hydroxymethyl-4-hydroxyphenyl)ethylamine (7)

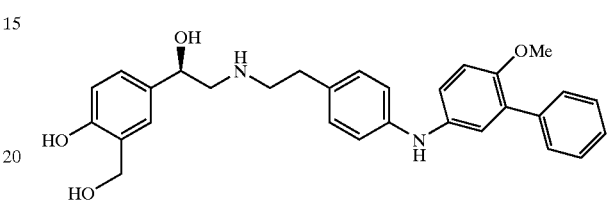

To 2.0 g (3.10 mmol) of compound H in 50 mL of ethanol was added 0.70 g of 10% palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 20 mL isopropanol, 1.65 mL of 4.0 N HCl in dioxane was added, and the product was precipitated by adding the solution to a large volume of diethyl ether. The solids were isolated by filtration to give 1.43 g (80%) of a hydrochloride salt of compound 7 as a white solid. $^1$H NMR (300 MHz, DMSO-d6) δ 9.4 (b, 1H), 9.01 (br s, 1H), 8.65 (br s, 1H), 7.39–7.22 (m, 6H), 6.99–6.83 (m, 8H), 6.69 (d, 1H), 5.45 (br, 4H), 4.77 (m, 1H), 4.39 (s, 2H), 3.62 (s, 3H), 3.02–2.78 (m, 6H); m/z: [M+H$^+$] calcd for C$_{30}$H$_{32}$N$_2$O$_4$ 485.24. found 485.4.

The intermediate compound H was prepared as follows.

a. Synthesis of Compound D.

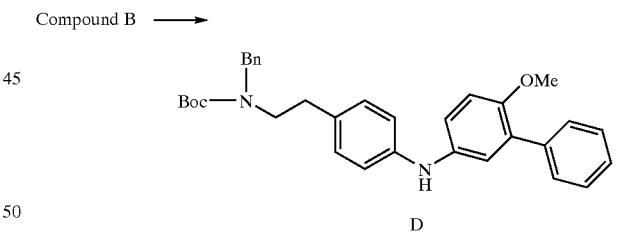

To a flask containing 3.91 g (10 mmol) of compound B (from Example 4, part b), 3.06 g (13 mmol) of 4-methoxy-3-phenylaniline hydrochloride (from TCI), 0.46 g (0.5 mmol) of tris(dibenzylidineacetone)dipalladium(0), 0.93 g (1.5 mmol) of rac-2,2'-bis(diphenylphosphino)-1,1'-binaphthyl, and 2.21 g (23 mmol) of sodium tert-butoxide was added 50 mL of toluene, and the mixture was heated at 95° C. for 5.5 hours under an nitrogen atmosphere. The mixture was partitioned between 1.0 M aqueous NaHSO$_4$ and diethyl ether, and the phases were separated. The diethyl ether phase was diluted with one volume of hexanes, and was washed once each with 1.0 M aqueous NaHSO$_4$ and brine, dried over Na$_2$SO$_4$, filtered, and concentrated to a dark oil. The oil was purified by silica gel chromatography, using 12% EtOAc/88% hexanes as eluant, to give 3.66 g (72%) of compound D as a yellow foam. $^1$H NMR (300 MHz, DMSO-d6) δ 7.76 (s, 1H), 7.38–7.13 (m, 10H), 6.95–6.81 (m, 7H), 4.28 (s, 2H), 3.61 (s, 3H), 3.16 (m, 2H), 2.53 (m, 2H), 1.29 (s, 9H).

b. Synthesis of Compound G.

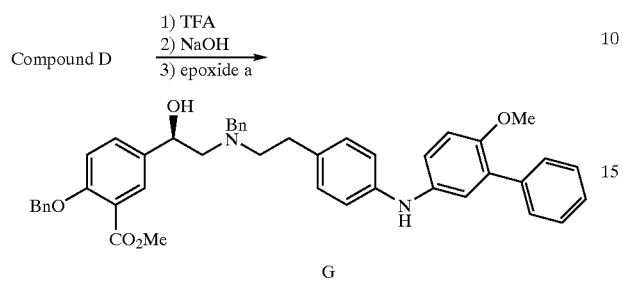

G

To 2.60 g (5.11 mmol) of compound D in 15 mL of CH$_2$Cl$_2$ at 0° C. was added 15 mL of trifluoroacetic acid. After 40 minutes, the solution was concentrated under reduced pressure, and the residue was partitioned between 1M aqueous NaOH and EtOAc. The phases were separated, and the EtOAc phase was washed once each with water and brine, dried over Na$_2$SO$_4$, filtered, and concentrated to an orange residue. The residue was dissolved in 15 mL of isopropanol, 1.45 g (5.11 mmol) of the epoxide a (Example 4, part d) was added, and the solution was heated at 78° C. overnight. The mixture was cooled to room temperature, and concentrated under reduced pressure to give compound G as an orange oil which was used in the next step without purification.

c. Synthesis of Compound H.

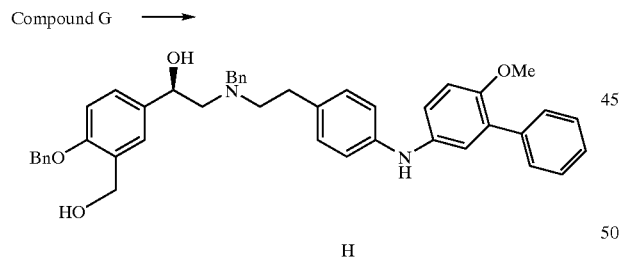

H

To 5.11 mmol of crude compound G from the previous step in 40 mL of tetrahydrofuran at 0° C. was added 12.7 mL (12.7 mmol) of 1.0 M lithium aluminum hydride in tetrahydrofuran. After 2 hours, the reaction was quenched by slow addition of sodium sulfate decahydrate. The slurry was diluted with diethyl ether, dried over Na$_2$SO$_4$, filtered, and concentrated to an orange oil. The oil was purified by chromatography, using 50% EtOAc/50% hexanes as eluent, to give 2.0 g (61%, 2 steps) of compound H as a white foam. $^1$H NMR (300 MHz, DMSO-d6) δ 7.72 (s, 1H), 7.38–6.77 (m, 25H), 5.00 (s, 2H), 4.92 (m, 1H), 4.65 (m, 1H), 4.55 (m, 1H), 4.45 (d, 2H), 3.62 (s, 2H), 3.61 (s, 3H), 2.52 (m, 6H).

Example 8

Synthesis of N-{2-[4-(3-phenyl-4-methoxyphenyl)aminophenyl]ethyl}-2-hydroxy-2-(8-hydroxy-2(1H)-quinolinon-5-yl)ethylamine (8)

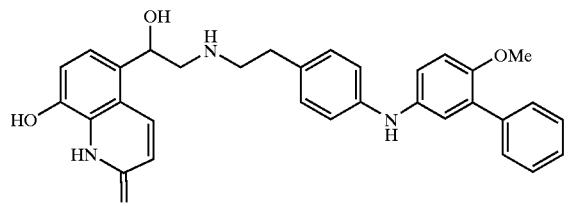

To a solution of 840 mg of compound S (1.2 mmol) in 40 mL of 1:1 methanol:THF was added 170 mg of 10% palladium on carbon. The reaction was shaken under an atmosphere of 35 psi H$_2$. After 24 h, the reaction was filtered and the filtrate purified by reversed-phase HPLC (gradient of 10 to 70% acetonitrile in 0.1% aqueous TFA). Fractions containing pure product were combined and lyophilized to afford a TFA salt of compound 8 as a powder.

A sample of the TFA salt (75 mg) was dissolved in acetonitrile (1.0 mL) and diluted with water (2.0 mL) followed by 0.1 N HCl (3.0 mL). The solution became cloudy. Addition of 1.5 mL acetonitrile afforded a clear solution which was frozen and lyophilized. The residue was redissolved in acetonitrile (1.0 mL) and diluted with water (2.0 mL) followed by 0.1 N HCl (4.0 mL). The solution became cloudy. Addition of 1.0 mL acetonitrile afforded a clear solution which was frozen and lyophilized. The hydrochloride salt of compound 8 (50 mg) was obtained as a gray solid. $^1$H NMR (300 MHz, DMSO-d6) δ 10.55 (br s, 1H), 9.30 (br s, 1H), 8.80, (br s, 1H), 8.24 (d, 1H), 7.25–7.48 (m, 5H), 6.92–7.18 (m 9H), 6.55 (d, 1H), 5.55 (d, 1H), 3.69 (s, 3H) 2.80–3.20 (m, 6H) m/z: [M+H$^+$] calcd for C$_{32}$H$_{31}$N$_3$O$_4$ 522.24. found 522.3.

The intermediate compound S was prepared as follows.

a. Synthesis of Compound S.

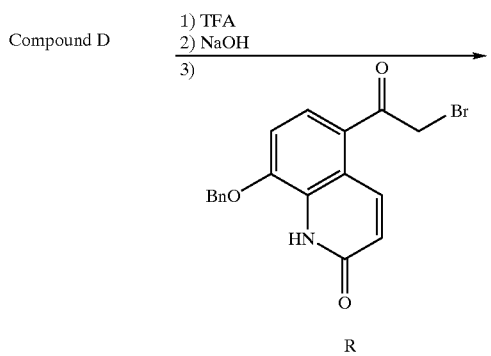

R

-continued

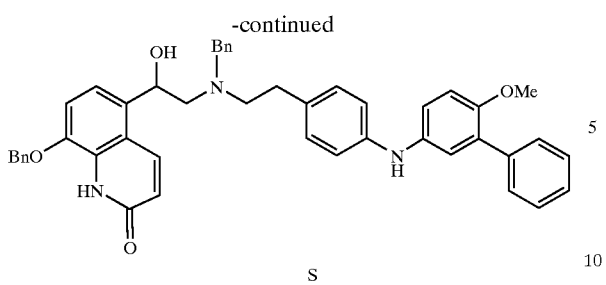

S

A solution of compound D (800 mg, 1.6 mmol, Example 7, part a) in 5 mL CH$_2$Cl$_2$ was cooled to 0° C. and 5 mL of TFA was added. After 20 min, the reaction was concentrated and the residue dissolved in ethyl acetate. The ethyl acetate solution was washed twice with 1.0 M aqueous NaOH followed by water and then dried over MgSO$_4$, filtered and concentrated to an oil. The oil was dissolved in 3 mL DMF and bromoketone R (800 mg, 2.1 mmol) and K$_2$CO$_3$ (650 mg, 4.7 mmol) were added. The reaction was heated to 40° C. After 1 h, the reaction was cooled and diluted with 5 mL methanol. NaBH$_4$ (150 mg, 4.0 mmol) was added and the reaction was stirred vigorously for 10 min. The reaction was quenched by dripping the suspension into 100 mL of rapidly stirred saturated aqueous NH$_4$Cl. Compound S precipitated and was isolated by filtration, washed with water and dried.

The intermediate bromoketone R can be prepared as described in Example 9B, parts a–d. See also EP 0 147 719 B.

Example 9A

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (9)

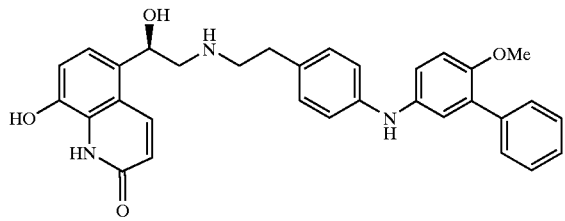

To a solution of 200 mg of compound T (0.28 mmol) in 4 mL of acetic acid was added 100 mg of 10% palladium on carbon. The reaction was shaken under an atmosphere of 40 psi H$_2$. After 17 h, the reaction was filtered and the filtrate purified by reversed-phase HPLC (gradient of 10 to 70% acetonitrile in 0.1% aqueous TFA). Fractions containing pure product were combined and lyophilized to afford compound 9 as a powder.

The intermediate compound T was prepared as follows:
a. Synthesis of Compound T

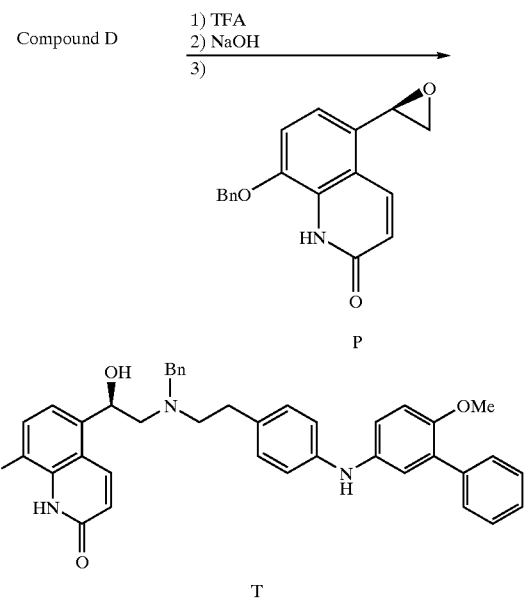

To 1.13 g of compound D (2.2 mmol, from Example 7, part a) in 4 mL CH$_2$Cl$_2$ was added 4 mL TFA. After 30 minutes, the solution was concentrated and diluted with 20 mL ethyl acetate and 20 mL water. The pH was raised to 11 by addition of 6.0 N aqueous sodium hydroxide and the layers were separated. The ethyl acetate layer was washed once with 1.0 N aqueous sodium hydroxide, dried over MgSO$_4$, filtered, and concentrated to a brown oil. The oil was dissolved in 7.0 mL of isopropanol and 600 mg (2.0 mmol) of epoxide P were added. The solution was heated to 70° C. After 34 h, the solution was concentrated and the product partially purified by silica gel chromatography (gradient of 1 to 2% methanol in CH$_2$Cl$_2$). Fractions containing product were combined and concentrated to afford T as a yellow oil.

Example 9B

Synthesis of N-{2-[4-(3-phenyl-4-methoxyphenyl)aminophenyl]ethyl}-(R)-2-hydroxy-2-(8-hydroxy-2(1H)-quinolinon-5-yl)ethylamine (9)

To a solution of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (4.0 g, 6.5 mmol) in tetrahydrofuran (100 mL) and water (16 mL) was added 10% palladium on carbon (800 mg). The reaction was stirred vigorously under one atmosphere of hydrogen for 6.5 h. The solids were filtered off and washed with tetrahydrofuran (4×25 mL) and then 50% methanol/tetrahydrofuran (2×25 mL). The combined filtrates were evaporated to dryness and the crude product was purified by reverse-phase HPLC. Fractions containing pure product were combined and lyophilized. The product from several runs was combined to give 4.68 g which was dissolved in acetonitrile (200 mL) and water (200 mL). 1.0 N HCl (18.7 mL) was added, and the solution was lyophilized. The residue was again dissolved in acetonitrile (125 mL) and water (125 mL). 1.0 N HCl was added and the solution was lyophilized to give a hydrochloride salt of compound 9 as an off white powder. $^1$H NMR (300 MHz, DMSO-d6) δ 10.55 (br s, 1H), 9.40 (br s, 1H), 8.80, (br s, 1H), 8.26 (d, 1H), 7.60, (br s, 2H) 7.25–7.45 (m, 5H), 6.92–7.16 (m 10H), 6.55 (d, 1H), 5.45 (d, 1H), 3.69 (s, 3H) 2.80–3.15 (m, 6H); m/z: [M+H⁺] calcd for $C_{32}H_{31}N_3O_4$ 522.24. found 522.4.

The intermediate PP was prepared as follows:

a. Synthesis of 8-acetoxy-2(1H)-quinolinone (CC)

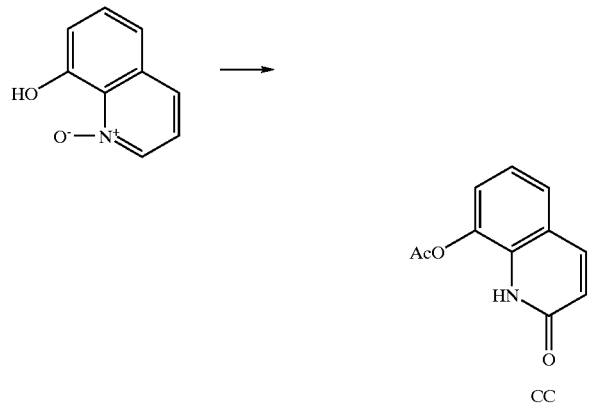

8-hydroxyquinoline-N-oxide (160.0 g, 1.0 mol) and acetic anhydride (800 mL, 8.4 mol) were heated at 100° C. for 3 hours and then cooled in ice. The product was collected on a Buchner funnel, washed with acetic anhydride (2×100 mL) and dried under reduced pressure to give 8-acetoxy-2(1H)-quinolinone (CC) (144 g) as a tan solid.

b. Synthesis of 5-acetyl-8-hydroxy-2(1H)-quinolinone (DD)

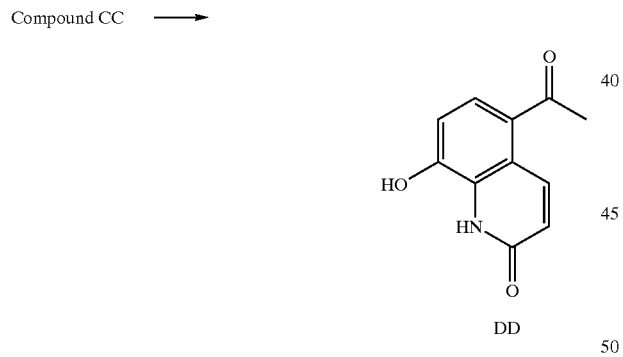

A slurry of aluminum chloride (85.7 g, 640 mmol) in 1,2-dichloroethane (280 mL) was cooled in ice, and compound CC (56.8 g, 280 mmol) was added. The mixture was warmed to room temperature, and then heated at 85° C. After 30 minutes acetyl chloride (1.5 mL, 21 mmol) was added and the mixture was heated an additional 60 minutes. The reaction mixture was then cooled and added to 1N HCl (3 L) at 0° C. with good stirring. After stirring for 2 hours, the solids were collected on a Buchner funnel, washed with water (3×250 mL) and dried under reduced pressure. The crude product isolated from several batches (135 g) was combined and triturated with dichloromethane (4 L) for 6 hours. The product was collected on a Buchner funnel and dried under reduced pressure to give 5-acetyl-8-hydroxy-2 (1H)-quinolinone (DD) (121 g).

c. Synthesis of 5-acetyl-8-benzyloxy-2(1H)-quinolinone (EE)

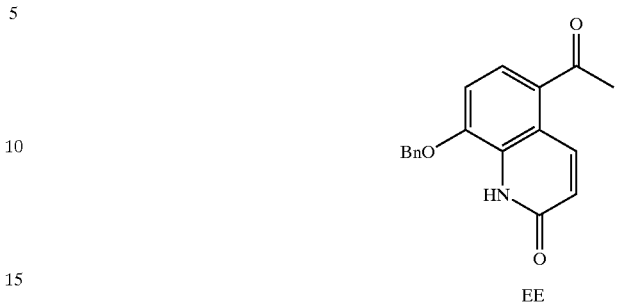

To 5-acetyl-8-hydroxy-2-quinolone (37.7 g, 186 mmol) was added dimethylformamide (200 mL) and potassium carbonate (34.5 g, 250 mmol) followed by benzyl bromide (31.8 g, 186 mmol). The mixture was stirred at room temperature for 2.25 hour and then poured into saturated sodium chloride (3.5 L) at 0° C. and stirred well for 1 hour. The product was collected and dried on a Buchner funnel for 1 hour, and the resulting solids were dissolved in dichloromethane (2 L) and dried over sodium sulfate. The solution was filtered through a pad of Celite and washed with dichloromethane (5×200 mL). The combined filtrate was then concentrated to dryness and the resulting solids were triturated with ether (500 mL) for 2 hours. The product was collected on a Buchner funnel, washed with ether (2×250 mL) and dried under reduced pressure to give 5-acetyl-8-benzyloxy-2(1H)-quinolinone (EE) (44 g) as an off white powder.

d. Synthesis of 5-(2-bromo-1-oxy)ethyl-8-benzyloxy-2 (1H)-quinolinone (R)

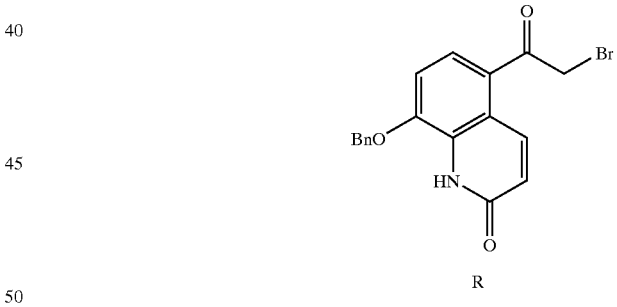

5-Acetyl-8-benzyloxy-2(1H)-quinolinone (EE) (20.0 g, 68.2 mmol) was dissolved in dichloromethane (200 mL) and cooled to 0° C. Boron trifluoride diethyl etherate (10.4 mL, 82.0 mmol) was added via syringe and the mixture was warmed to room temperature to give a thick suspension. The suspension was heated at 45° C. (oil bath) and a solution of bromine (11.5 g, 72.0 mmol) in dichloromethane (100 mL) was added over 40 minutes. The mixture was kept 45° C. for an additional 15 minutes and then cooled to room temperature. The mixture was concentrated under reduced pressure and then triturated with 10% aqueous sodium carbonate (200 mL) for 1 hour. The solids were collected on a Buchner funnel, washed with water (4×100 mL) and dried under reduced pressure. The product of two runs was combined for purification. The crude product (52 g) was triturated with 50% methanol in chloroform (500 mL) for 1 hour. The product was collected on a Buchner funnel and washed with 50% methanol in chloroform (2×50 mL) and methanol (2×50 mL). The solid was dried under reduced pressure to give 5-(2-bromo-1-oxy)ethyl-8-benzyloxy-2(1H)-quinolinone (R) (34.1 g) as an off white powder.

e. Synthesis of 5-(2-bromo-(R)-1-hydroxy)ethyl-8-benzyloxy-2(1H)-quinolinone (FF)

Compound R ⟶

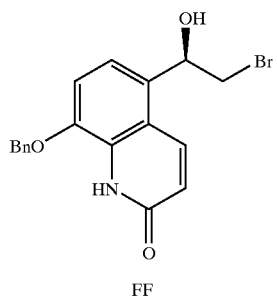

FF

Using a procedure described in Mathre et al., *J. Org. Chem.,* 1991, 56, 751–762, a catalyst was prepared as follows. (R)-(+)-α,α-Diphenylprolinol (10.0 g, 39 mmol) and trimethylboroxine (3.7 mL, 26 mmol) were combined in toluene (200 mL) and stirred at room temperature for 30 min. The mixture was placed in a 150° C. oil bath and 150 mL liquid was distilled away. Toluene (50 mL) was added, and another 50 mL of distillate was collected. Another portion of toluene (50 mL) was added and a further 50 mL of distillate was collected. A 1.00 mL aliquot of the material remaining in the pot was evaporated to dryness and weighed (241.5 mg) to determine that the concentration of catalyst was 0.87 M.

5-(2-Bromo-1-oxy)ethyl-8-benzyloxy-2(1H)-quinolinone (R) (30.0 g, 81 mmol) was suspended in, tetrahydrofuran (1.2 L) under a nitrogen atmosphere and the catalyst from above (13 mL, 11 mmol) was added. The suspension was cooled to −5° C. in an ice/isopropanol bath and borane (1.0 M in THF, 97 mL, 97 mmol) was added over 3 h. The reaction was stirred an additional 45 min at −5° C., then methanol (200 mL) was added slowly. The mixture was concentrated under vacuum to give 5-(2-bromo-(R)-1-hydroxy)ethyl-8-benzyloxy-2(1H)-quinolinone (FF).

f. Synthesis of 5-(2-bromo-(R)-1-tert-butyldimethylsiloxy)ethyl-8-benzyloxy-2(1H)-quinolinone (HH)

Compound FF ⟶

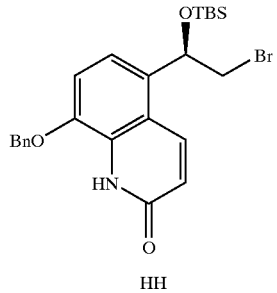

HH

Compound FF (15 g, 40 mmol) and 2,6-lutidine (9.3 mL, 80 mmol) were suspended in dichloromethane at 0° C. tert-Butyldimethylsilyl trifluoromethane sulfonate (18.5 mL, 80 mmol) was added dropwise. The mixture was allowed to warm to room temperature and stirred overnight. The reaction was diluted with dichloromethane (200 mL) and washed twice with 1N hydrochloric acid, then three times with brine. The organics were dried over magnesium sulfate and the volume was reduced to 100 mL under vacuum. The organics were applied to a silica gel column equilibrated with 30% ethyl acetate in hexanes and the product was eluted with 50% ethyl acetate in hexanes. Removal of the solvent under reduced pressure gave 5-(2-bromo-(R)-1-tert-butyldimethylsiloxy)ethyl-8-benzyloxy-2 (1H)-quinolinone (HH). (10.3 g). Unreacted starting material (compound FF, 2 g) was also recovered.

g. Synthesis of N-tert-butoxycarbonyl-2-[4-(3-[phenyl-4-methoxyphenyl)aminophenyl]ethylamine (LL)

Compound X +

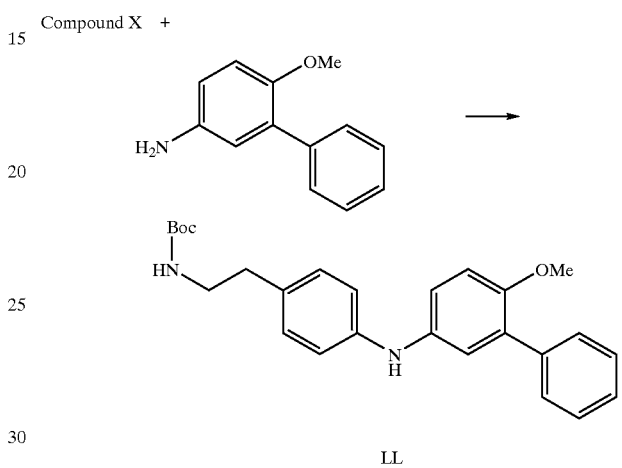

LL

Under nitrogen, compound X (example 6 part a) (5.0 g, 16.7 mmol) was mixed with toluene (80 mL) and 4-methoxy-3-phenylaniline hydrochloride (4.3 g, 18.3 mmol) was added to form a slurry. 2,2'-Bis (diphenylphosphino)-1,1'-binaphthyl (1.6 g, 2.5 mmol) was added, followed by tris(dibenzylideneacetone)dipalladium (0) (760 mg, 0.83 mmol) and finally sodium tert-butoxide (5.3 g, 55 mmol). The mixture was heated at 90° C. for 150 min and then cooled to room temperature. Water (150 mL) was added followed by ethyl acetate (150 mL) and the phases partitioned. The aqueous layer was extracted with ethyl acetate (150 mL) and the combined organics washed three times with 0.5 M sodium bisulfate (200 mL), once with saturated sodium bicarbonate (150 mL) and twice with saturated sodium chloride (150 mL). The organics were dried over magnesium sulfate (50 g) and the volatiles removed under vacuum to give N-tert-butoxycarbonyl-2-[4-(3-[phenyl-4-methoxyphenyl)aminophenyl]ethylamine (LL) (8.4 g) which was used without further purification.

h. Synthesis of 2-[4-(3-[phenyl-4-methoxyphenyl) aminophenyl]ethylamine (MM)

Compound LL ⟶

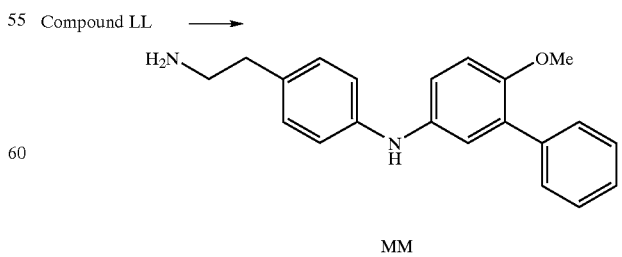

MM

Under nitrogen, compound LL (94.6 g) was treated with dichloromethane (500 mL) and cooled in an ice bath.

Hydrogen chloride (4 M in dioxane, 125 mL, 500 mmol) was added in 10 portions over 20 min. The reaction was kept at room temperature for 130 minutes, during which time the product precipitated. The solid was filtered, washed with dichloromethane (350 mL) and dried under vacuum in the dark to give the dihydrochloride salt of 2-[4-(3-[phenyl-4-methoxyphenyl)aminophenyl]ethylamine (MM) (37.1 g). $^1$H NMR (300 MHz, DMSO-d6) δ 8.29 (br s, 2H), 8.04 (br s, 1H) 7.25–7.50 (m, 5H), 6.90–7.08 (m, 7H) 3.69 (s, 3H), 2.93 (m, 2H), 2.75 (m, 2H); m/z: [M+H$^+$] calcd for $C_{21}H_{22}N_2O$ 319.18. found 319.3.

i. Synthesis of N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN)

Compounds HH + MM ⟶

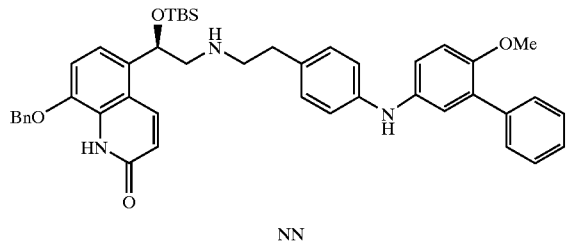

NN

The dihydrochloride salt of compound MM was partitioned between isopropyl acetate and 1.0 N sodium hydroxide. The organic layer was dried over sodium sulfate and concentrated to give the free base as a dark oil.

Sodium iodide (4.2 g, 28 mmol), compound HH (9.1 g, 18.6 mmol) and sodium bicarbonate (4.7 g, 55.9 mmol), were weighed into a flask. Under nitrogen, compound MM (7 g, 22 mmol) in dimethyl sulfoxide (20 mL) was added and the mixture stirred at 140° C. (oil bath) for 30 min, then cooled to room temperature. Ethyl acetate was added (200 mL) and the mixture washed three times with 1N hydrochloric acid, then with 1N sodium hydroxide, saturated sodium bicarbonate and finally saturated sodium chloride (200 mL each). The organics were dried over sodium sulfate and evaporated to dryness to give N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN) (13.9 g) which was used in the next step without further purification.

j. Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Compound NN ⟶

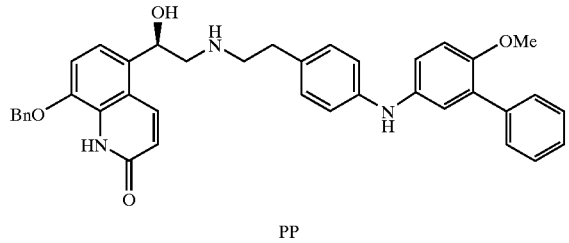

PP

Compound NN (13.9 g) was combined with methanol (200 mL) and concentrated hydrochloric acid (170 mL) was added in portions (exothermic). The solution turned orange and cloudy after the addition and more methanol (100 mL) was added until a clear solution was obtained. The mixture was stirred at room temperature overnight, in which time a brown gum had formed. The solvent was removed under vacuum, and ethyl acetate (300 mL) was added. The resulting mixture was cooled in an ice bath, and neutralized (pH 7) with 10 N sodium hydroxide. The pH was then raised to 10 with 1 M sodium hydroxide to give a clear biphasic mixture. The phases were separated and the aqueous layer was extracted with ethyl acetate (300 mL). The combined organic layers were dried over sodium sulfate, and evaporated to dryness. The crude product was purified by flash chromatography on silica gel (500 g, 0–10% methanol in dichloromethane) to give N-{2-[4-(3-phenyl-4-methoxyphenyl)aminophenyl]ethyl}-(R)-2-hydroxy-2-(8-benzyloxy-2(1H)-quinolinon-5-yl)ethylamine (PP) (5.6 g).

Example 9C

Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

The intermediate compound PP was prepared as follows:

a. Synthesis of 5-(2-bromo-(R)-1-hydroxy)ethyl-8-benzyloxy-2(1H)-quinolinone (FF)

(R)-(+)-α,α-Diphenylprolinol (30.0 g, 117 mmol) and trimethylboroxine (11.1 mL, 78 mmol) were combined in toluene (300 mL) and stirred at room temperature for 30 minutes. The mixture was placed in a 150° C. oil bath and liquid was distilled off. Toluene was added in 20 mL aliquots, and distillation was continued for 4 hours. A total of 300 mL toluene was added. The mixture was finally cooled to room temperature. A 500 μL aliquot was evaporated to dryness, weighed (246 mg) to determine that the concentration of catalyst was 1.8 M.

5-(2-Bromo-1-oxy)ethyl-8-benzyloxy-2(1H)-quinolinone (R) (90.0 g, 243 mmol) was placed under nitrogen, tetrahydrofuran (900 mL) was added followed by the catalyst from above (1.8 M in toluene, 15 mL, 27 mmol). The suspension was cooled to −10±5° C. in an ice/isopropanol bath. Borane (1.0 M in THF, 294 mL, 294 mmol) was added over 4 hours. The reaction was stirred an additional 45 minutes at −10° C., then methanol (250 mL) was added slowly. The mixture was concentrated under vacuum. The residue was dissolved in boiling acetonitrile (1.3 L), filtered while hot and cooled to room temperature. The crystals were filtered, washed with acetonitrile and dried under vacuum to give 5-(2-bromo-(R)-1-hydroxy)ethyl-8-benzyloxy-2(1H)-quinolinone (FF) (72.5 g, 196 mmol, 81% yield, 95% ee, 95% pure by HPLC area ratio).

b. Synthesis of 5-(2-bromo-(R)-1-tert-butyldimethylsiloxy)ethyl-8-benzyloxy-2(1H)-quinolinone (HH)

Compound FF (70.2 g, 189 mmol) was treated with N,N-dimethylformamide (260 mL) and cooled in an ice bath under nitrogen. 2,6-Lutidine (40.3 g, 376 mmol) was added over 5 minutes followed slowly by tert-butyldimethylsilyl trifluoromethanesulfonate (99.8 g, 378 mmol), keeping the temperature below 20° C. The mixture was allowed to warm to room temperature for 45 minutes. Methanol (45 mL) was added to the mixture dropwise over 10 minutes and the mixture was partitioned between ethyl acetate/cyclohexane (1:1, 500 mL) and water/brine (1:1, 500 mL). The organics were washed twice more with water/brine (1:1, 500 mL each). The combined organics were evaporated under reduced pressure to give a light yellow oil. Two separate portions of cyclohexane (400 mL) were added to the oil and distillation continued until a thick white slurry was formed. Cyclohexane (300 mL) was added to the slurry and the resulting white crystals were filtered, washed with cyclohexane (300 mL) and dried under reduced pressure to give 5-(2-bromo-(R)-1-tert-butyldimethylsiloxy)ethyl-8-benzyloxy-2(1H)-quinolinone (HH) (75.4 g, 151 mmol, 80% yield, 98.6% ee).

c. Synthesis of N-[2-(4-bromophenyl)ethyl]-(R)-2-tert-butyldimethylsiloxy-2-(8-benzyloxy-2(1H)-quinolinon-5-yl)ethylamine (JJ)

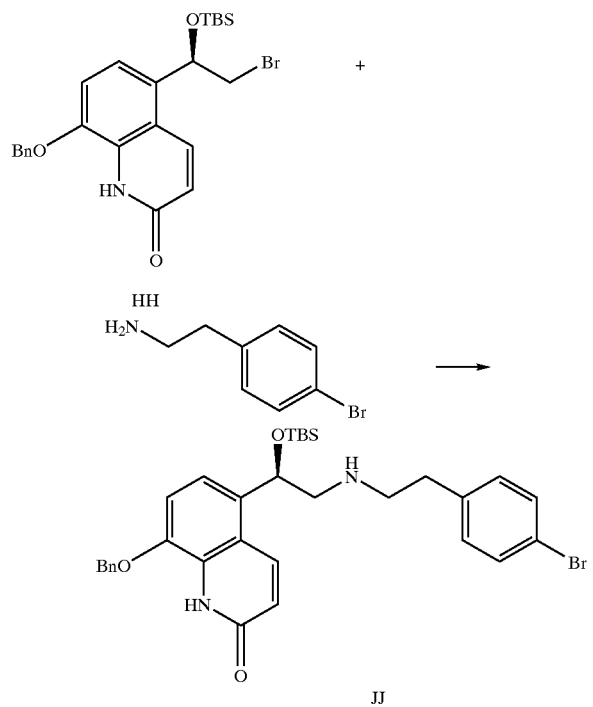

Compound HH (136.5 g, 279 mmol), 4-bromophenethylamine (123 g, 615 mmol) and dimethyl sulfoxide (180 mL) were mixed at room temperature under nitrogen. Another 40 mL of dimethyl sulfoxide was added. The mixture was heated to 85° C. for 5 hours. The reaction was partitioned between ethyl acetate (1 L) and 10% aqueous acetic acid (500 mL). The organics were washed with 10% aqueous acetic acid (3×500 mL), then with 1N sodium hydroxide (3×500 mL). The last wash was filtered through Celite (100 g). The organic layer was concentrated to 300 mL and cyclohexane (2×500 mL) was added and the solution concentrated to 300 mL. Sufficient cyclohexane was added to form 1.8 L final volume which was filtered through Celite (50 g). A solution of HCl in isopropanol, prepared by slowly adding concentrated HCl (23.5 mL) to isopropanol (180 mL) at 10° C. (internal), was added to the crude product and the reaction mixture was stirred for 5 hours, washed with cyclohexane (2×500 mL) and dried under reduced pressure for 24 hours to give N-[2-(4-bromophenyl)ethyl]-(R)-2-tert-butyldimethylsiloxy-2-(8-benzyloxy-2(1H)-quinolinon-5-yl)ethylamine (JJ) hydrochloride (145 g, 80 mol %, 106 wt %, HPLC purity 97.9%).

d. Synthesis of N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN)

To compound JJ hydrochloride (73.7 g, 114 mmol) and 4-methoxy-3-phenylaniline hydrochloride (32.4 g, 137 mmol), toluene (380 mL) was added with mild agitation for 5 minutes, followed by sodium tert-butoxide (49.3 g, 513 mmol) in portions over 1 minute, and finally 2,2'-bis(diphenylphosphino)-1,1'-binaphthyl (10.65 g, 17 mmol) and tris(dibenzylideneacetone)dipalladium(0) (5.22 g, 5.7 mmol). The resulting mixture was stirred and heated to 85–89° C. (internal) for 2.5 hours. The solution was cooled to room temperature, water (400 mL) was added and the mixture was stirred for 5 minutes, filtered through Celite (80 g), and partitioned with toluene (100 mL). The organic layer was collected and concentrated under reduced pressure in a 40° C. bath to give N-{2-[4-(3-phenyl-4-methoxyphenyl)aminophenyl]ethyl}-(R)-2-tert-butyldimethylsilyl-2-(8-benzyloxy-2(1H)-quinolinon-5-yl)ethylamine (NN) as a dark viscous oil.

e. Synthesis of N-{2-[4-(3-phenyl-4-methoxyphenyl)aminophenyl]ethyl}-(R)-2-hydroxy-2-(8-benzyloxy-2(1H)-quinolinon-5-yl)ethylamine (PP)

Compound NN from the previous step was dissolved in 280 ml of THF. Triethylamine trihydrofluoride (27.6 g, 171 mmol) was added to the solution, an additional 20 mL of THF was used to rinse down residual reagent, and the reaction was stirred at 25° C. under nitrogen for 16 hours. The reaction mixture was concentrated under reduced pressure in a 25° C. bath to give a dark viscous oil to which dichloromethane (400 mL) was added, followed by 1N aqueous NaOH (200 mL). The reaction mixture was stirred for 5 hours. The top layer was discarded and the organic layer was concentrated to a viscous oil.

The oil was dissolved in dichloromethane to give a total volume of 630 mL. A 60 mL aliquot was taken and concentrated to 30 mL. Toluene (60 mL) was added, followed by a mixture of concentrated hydrochloric acid (2.7 mL) and methanol (4.5 mL) to give a thick paste covered in a free-flowing liquid. The liquid was carefully removed and the paste washed with toluene (50 mL). The gum was partitioned between dichloromethane (40 mL) and 1N aqueous sodium hydroxide (40 mL) and the organic solvents were removed under reduced pressure. The residue was purified chromatographically over silica using a gradient of 0–10% methanol in dichloromethane to give N-{2-[4-(3-phenyl-4-methoxyphenyl)aminophenyl]ethyl}-(R)-2-hydroxy-2-(8-benzyloxy-2(1H)-quinolinon-5-yl)ethylamine (PP).

Example 10

Synthesis of N-{2-[4-(3-phenyl-4-ethoxyphenyl)aminophenyl]ethyl}-(R)-2-hydroxy-2-(3-hydroxymethyl-4-hydroxyphenyl)ethylamine (10)

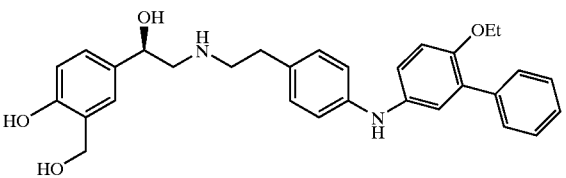

To a mixture of 825 mg (1.22 mmol) of compound N in 15 mL of ethanol was added 260 mg of 10% palladium on carbon under a stream of nitrogen. The flask was fitted with a balloon of hydrogen gas, and the reaction was vigorously stirred for 3 hours. The reaction was filtered through celite, using methanol to rinse, and the filtrate was concentrated under reduced pressure. The residue was dissolved in 10 mL isopropanol, 0.67 mL of 4.0 N HCl in dioxane was added, and the product was precipitated by adding the solution to a large volume of EtOAc. The solids were isolated by filtration to give a hydrochloride salt of compound 10 as a white solid. m/z: [M+H$^+$] calcd for $C_{31}H_{34}N_2O_4$ 499.26. found 499.3.

The intermediate compound N was prepared as follows.

a. Synthesis of Compound J.

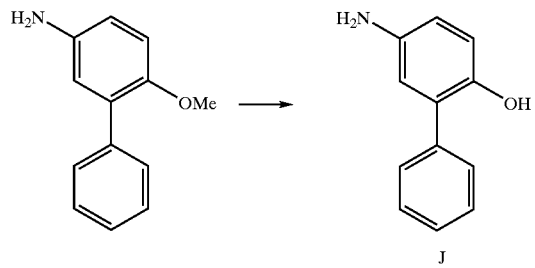

J 4.84 g (20.5 mmol) of 4-methoxy-3-phenylaniline hydrochloride (available from TCI) was partitioned between diethyl ether and 1.0 M aqueous NaOH, and the phases were separated. The diethyl ether phase was washed once each with water and brine, dried over $K_2CO_3$, filtered, and concentrated to a brown solid. The solid was dissolved in 100 mL of $CH_2Cl_2$, the solution was cooled to 0° C., and 21.2 g (84.6 mmol) of boron tribromide was added. After 20 minutes, the reaction was poured over 500 mL of ice, and the mixture was stirred overnight. The mixture was washed twice with EtOAc to remove oxidized material, and the EtOAc phases were discarded. The acidic phase was basified with solid $NaHCO_3$, and was extracted twice with EtOAc. The combined EtOAc phases were washed once with brine, dried over $Na_2SO_4$, filtered, and concentrated to give 2.48 g of compound J as a brown solid. $^1$H NMR (300 MHz, DMSO-d6) δ 8.37 (s, 1H), 7.41–7.14 (m, 5H), 6.57–6.32 (m, 3H), 4.45 (s, 2H).

b. Synthesis of Compound K.

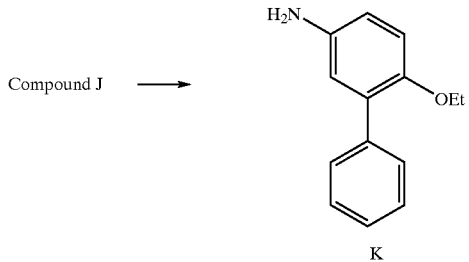

K

To 2.28 g (12.2 mmol) of compound J in 45 mL of dimethylformamide at 0° C. was added 734 mg (18.4 mmol) of 60% NaH in oil. After 10 minutes, 1.90 g (12.2 mmol) of iodoethane was added. After 20 minutes, the solution was partitioned between diethyl ether and 5% aqueous $Na_2SO_3$, and the phases were separated. The diethyl ether phase was washed once each with 1.0 M aqueous NaOH, water, and brine, dried over $Na_2SO_4$, and concentrated to give compound K as a dark brown oil. $^1$H NMR (300 MHz, DMSO-d6) δ 7.37–7.19 (m, 5H), 6.73 (d, 1H), 6.47–6.42 (m, 2H), 4.65 (s, 2H), 3.73 (q, 2H), 1.07 (t, 3H).

c. Synthesis of Compound L.

Comppounds B + K ⟶

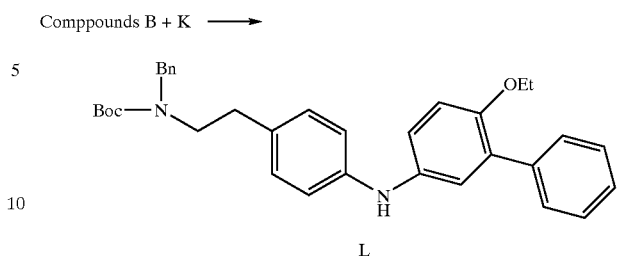

L

To a flask containing 3.97 g of compound B (10.7 mmol, Example 4, part b), 2.27 g (12.2 mmol) of compound K, 0.46 g (0.5 mmol) of tris(dibenzylidine-acetone)dipalladium(0), 0.95 g (1.5 mmol) of rac-2,2'-bis(diphenylphosphino)-1,1'-binaphthyl, and 1.27 g (13.3 mmol) of sodium tert-butoxide was added 48 mL of toluene, and the mixture was heated at 95° C. for 5.5 hours under an nitrogen atmosphere. The mixture was partitioned between 1.0 M aqueous $NaHSO_4$ and diethyl ether, and the phases were separated. The diethyl ether phase was diluted with one volume of hexanes, and was washed once each with 1.0 M aqueous $NaHSO_4$ and brine, dried over $Na_2SO_4$, filtered, and concentrated to a dark oil. The oil was purified by silica gel chromatography, using 10% EtOAc/90% hexanes as eluant, to give 4.13 g (77%) of compound L as a yellow foam. $^1$H NMR (300 MHz, DMSO-d6) δ 7.76 (s, 1H), 7.42–7.13 (m, 10H), 6.93–6.81 (m, 7H), 4.27 (s, 2H), 3.86 (q, 2H), 3.25 (m, 2H), 2.53 (m, 2H), 1.28 (s, 9H), 1.13 (t, 3H).

d. Synthesis of Compound M.

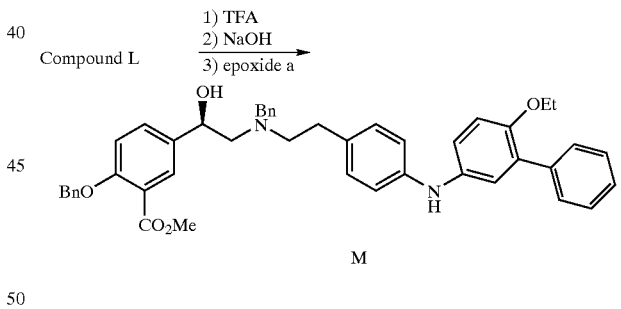

M

To 1.40 g (2.68 mmol) of compound L in 15 mL of $CH_2Cl_2$ at 0° C. was added 15 mL of trifluoroacetic acid. After 40 minutes, the solution was concentrated under reduced pressure, and the residue was partitioned between 1.0 M aqueous NaOH and EtOAc. The phases were separated, and the EtOAc phase was washed once each with water and brine, dried over $Na_2SO_4$, filtered, and concentrated to an orange residue. The residue was dissolved in 15 mL of isopropanol, 1.45 g (2.68 mmol) of the epoxide a (Example 4, part d) was added, and the solution was heated at 78° C. overnight. The mixture was cooled to room temperature, and concentrated under reduced pressure to give an orange oil that was used in the following step without analysis.

e. Synthesis of Compound N.

Compound M ⟶

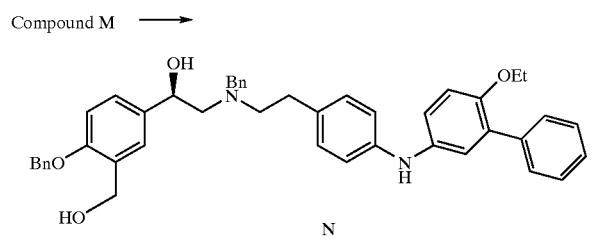

N

To 2.68 mmol of crude compound M in 20 mL of tetrahydrofuran at 0° C. was added 7.0 mL (7.0 mmol) of 1.0 M lithium aluminum hydride in tetrahydrofuran. After 2 hours, the reaction was quenched by slow addition of sodium sulfate decahydrate. The slurry was diluted with diethyl ether, dried over $Na_2SO_4$, filtered, and concentrated to an orange oil. The oil was purified by silica gel chromatography, using 50% EtOAc/50% hexanes as eluent, to give 835 mg of compound N as a white foam. $^1$H NMR (300 MHz, DMSO-d6) δ 7.73 (s, 1H), 7.42–6.77 (m, 25H), 5.00 (s, 2H), 4.93 (m, 1H), 4.66 (d, 1H), 4.51 (m, 1H), 4.47 (m, 2H), 3.86 (q, 2H), 3.62 (m, 2H), 2.55 (m, 6H), 1.13 (t, 3H).

Example 11

Synthesis of N-{2-[4-(3-phenyl-4-ethoxyphenyl)aminophenyl]ethyl}-(R)-2-hydroxy-2-(3-formamido-4-hydroxyphenyl)ethylamine (11)

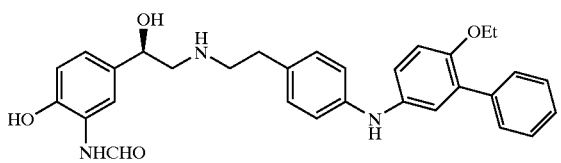

To a mixture of 746 mg (1.07 mmol) of compound O in 15 mL of ethanol and 5 mL of EtOAc was added 260 mg of 10% palladium on carbon under a stream of nitrogen. The flask was fitted with a balloon of hydrogen gas, and the reaction was vigorously stirred for 3 hours. The reaction was filtered through celite, using methanol to rinse, and the filtrate was concentrated under reduced pressure. The residue was dissolved in 20 mL isopropanol, 0.58 mL of 4.0 N HCl in dioxane was added, and the product was precipitated by adding the solution to a large volume of EtOAc. The solids were isolated by filtration to give a hydrochloride salt of compound 11 as an off white solid. $^1$H NMR (300 MHz, DMSO-d6) δ 10.12 (br s, 1H), 9.62 (s, 1H), 8.90 (br s, 1H), 8.67 (br s, 1H), 8.27 (d, 1H), 8.14 (d, 1H), 7.25 (m, 5H) 6.85–7.08 (m, 9H), 4.80 (dd, 1H), 3.94 (quar, 2H), 2.75–3.15 (m, 6H), 1.21 (t, 3H); m/z: [M+H$^+$] calcd for $C_{31}H_{33}N_3O_4$ 512.25. found 512.5.

The intermediate compound O was prepared as follows.
a. Synthesis of Compound O.

Compound L  1) TFA
2) NaOH
3)

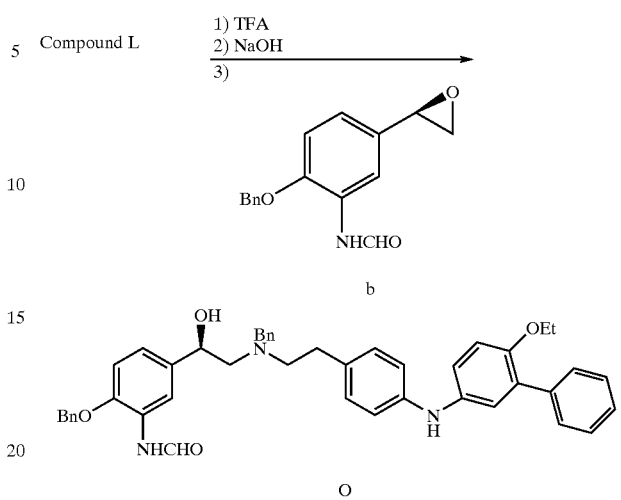

To 1.4 g (2.68 mmol) of compound L (Example 10, part c) in 6 mL of $CH_2Cl_2$ at 0° C. was added 6 mL of trifluoroacetic acid. After 40 minutes, the solution was concentrated under reduced pressure, and the residue was partitioned between 1.0 M aqueous NaOH and EtOAc. The phases were separated, and the EtOAc phase was washed once each with water and brine, dried over $Na_2SO_4$, filtered, and concentrated to an orange residue. The residue was dissolved in 5 mL of isopropanol, 721 mg (2.68 mmol) of the epoxide b was added, and the solution was heated at 78° C. overnight. The mixture was cooled to room temperature, and concentrated under reduced pressure to give an orange oil. The oil was purified by silica gel chromatography using 50 EtOAc/50 hexanes as eluent, to give 756 mg of compound O as a white foam. $^1$H NMR (300 MHz, DMSO-d6) δ 9.45 (d, 1H), 8.25 (d, 1H), 8.14 (d, 1H), 7.72 (s, 1H), 7.45–6.76 (m, 25H), 5.10 (s, 2H), 5.04 (m, 1H), 3.94 (q, 2H), 3.61 (s, 2H), 2.50 (s, 6H), 1.13 (t, 3H).

The intermediate epoxide b can be prepared as described in U.S. Pat. No. 6,268,533 B1; and in R. Hett et al., *Organic Process Research and Development*, 1998, 2, 96–99.

Example 12

Synthesis of N-{2-[4-(3-phenylphenyl)aminophenyl]ethyl}-(R)-2-hydroxy-2-(8-hydroxy-2(1H)-quinolinon-5-yl)ethylamine (12)

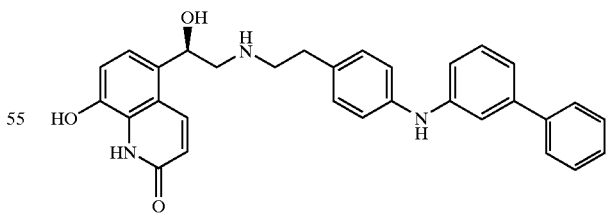

Compound W (55.2 mg, 0.094 mmol), phenyl boronic acid (13.2 mg, 0.113 mmol) and [1,1'-bis(diphenylphosphinoferrocene)dichloropalladium (II), complex with dichloromethane ($PdCl_2$(dppf)-DCM) (5.0 mg, 0.006 mmol) were combined in a small pressure tube and purged with $N_2$. 1,2-Dimethoxyethane (1.0 mL) and 2.0 N cesium carbonate (150 μL, 0.3 mmol) were added. The tube was sealed, and then placed in an oil bath at 90° C. for 4 hours. The solution was then cooled to room temperature and DCM (10 mL) was added. The solution was filtered and concentrated to dryness. To the residue there was added DMF (1.0 mL), 10% Pd/C (100 mg) and ammonium formate (200 mg) and the solution was heated to 50° C. for 1.5 hours. At this time, water:acetonitrile 1:1 and 200 μL TFA was added and the solution was filtered to remove the catalyst. The filtrate was purified by reverse phase HPLC. Fractions containing pure product were combined and lyophilized to give compound 12 as a TFA salt. $^1$H NMR (300 MHz, DMSO-d6) δ 10.46 (s, 1H), 10.39 (s, 1H), 8.60 (br s, 2H), 8.19 (s, 1H), 8.07 (d, 1H), 7.50 (d, 2H), 7.37 (t, 2H) 7.15–7.30 (m, 3H), 6.85–7.10 (m, 9H), 6.51 (dd, 1H), 6.11 (d, 1H), 5.23 (d, 1H), 2.70–3.15 (m, 6H); m/z: [M+H$^+$] calcd for $C_{31}H_{29}N_3O_3$ 492.23. found 492.3.

a. Synthesis of Compound U

Compound HH ⟶

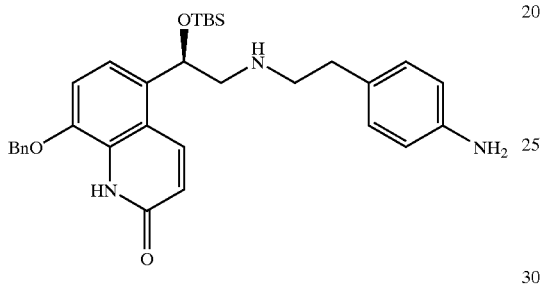

U

Compound HH (Example 9B, part f) (9.1 g, 18.62 mmol), 4-aminophenethylamine (9.8 mL, 74.8 mmol) and sodium iodide (4.2 g, 27.93 mmol) were placed in a flask and purged with nitrogen. Methyl sulfoxide (25 mL) was added, and the solution was placed in an oil bath heated at 140° C. The solution was the stirred for 20 min at 140° C. The reaction was allowed to cool to room temperature, then ethyl acetate (300 mL) and H$_2$O (300 mL) were added. The phases were partitioned, and the organic layer was washed with water (4×200 mL) and saturated sodium chloride (4×200 mL). The organic phase was dried over sodium sulfate, filtered and concentrated under vacuum to yield compound U (10.5 g).

b. Synthesis of Compound W

Compound U ⟶

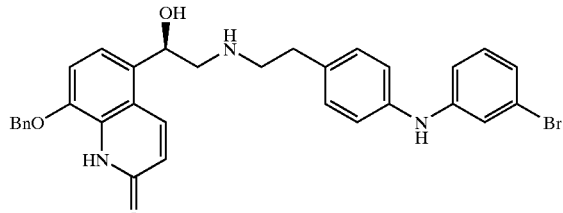

W

Compound U (5.18 g, 9.53 mmol), tris(dibenzylideneacetone)dipalladium(0) (0.44 g, 0.48 mmol), 2,2′-bis(diphenylphosphino)-1,1′-binaphthyl (0.63 g, 0.95 mmol), and sodium t-butoxide (1.83 g, 19.06 mmol) were combined in a flask and purged with nitrogen. 1-Bromo-3-iodobenzene (2.0 mL, 11.44 mmol) was added and the flask was purged again. o-Xylene (50 mL) was added, and the solution was heated at reflux under nitrogen for 2.5 hours, at which time HPLC analysis indicated complete reaction. The o-xylene was removed under vacuum with heating, and dichloromethane (200 mL) was added. Once the residue was dissolved, celite (30 g) was added, and the mixture was filtered and filter cake was washed with dichloromethane until all of the product was collected. The solution was concentrated to dryness under vacuum, redissolved in THF (20 mL), and purged with nitrogen. Tetrabutylammonium fluoride (20 mL, 1.0 M in THF, 20 mmol) was added via syringe, and the solution was stirred for 18 hours at room temperature. The THF was then removed, and the residue was dissolved in DCM, and washed with water (1×200 mL) and half-saturated sodium chloride (1×200 mL). The organic phase was dried over sodium sulfate, concentrated and chromatographed over silica gel (50 g, 0–10% MeOH in dichloromethane) to yield compound W as a yellow solid.

Example 13

Synthesis of N-{2-[4-(3-phenyl-4-methoxyphenyl)aminophenyl]ethyl}-(R)-2-hydroxy-2-(3-formamido-4-hydroxyphenyl)ethylamine (13)

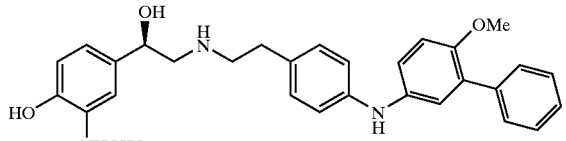

To a mixture of 1.24 g (1.83 mmol) of compound I in 30 mL of ethanol and 20 mL of methanol was added 400 mg of 10% palladium on carbon under a stream of nitrogen. The flask was fitted with a balloon of hydrogen gas, and the reaction was vigorously stirred for 1.5 hours. The reaction was filtered through celite, using methanol to rinse, and the filtrate was concentrated under reduced pressure. The residue was dissolved in 20 mL isopropanol, 0.21 mL of 4.0 N HCl in dioxane was added, and the product was precipitated by adding the solution to a large volume of EtOAc. The solids were isolated by filtration to give 447 mg of a hydrochloride salt of compound 13 as a white solid. $^1$H NMR (300 MHz, DMSO-d6) δ 10.03 (br s, 1H), 9.55 (s, 1H), 8.81 (br s, 1H), 8.59 (br s, 1H), 8.20 (d, 1H), 8.07 (d, 1H), 7.39–7.20 (m, 5H), 6.99–6.79 (m, 10H), 4.75 (m, 1H), 3.62 (s, 3H), 3.03–2.72 (m, 6H); m/z: [M+H$^+$] calcd for $C_{30}H_{31}N_3O_4$ 498.24. found 498.5.

The intermediate compound I was prepared as follows.

a. Synthesis of Compound I.

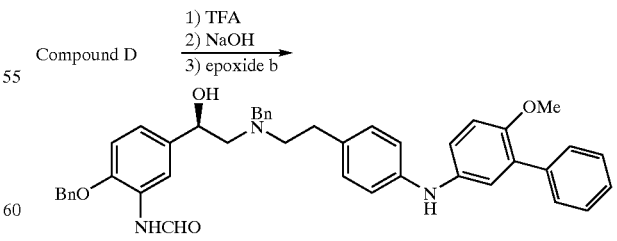

I

To 944 mg (1.85 mmol) of compound D (Example 7, part a) in 6 mL of CH$_2$Cl$_2$ at 0° C. was added 6 mL of trifluoroacetic acid. After 40 minutes, the solution was concentrated under reduced pressure, and the residue was partitioned between 1.0 M aqueous NaOH and EtOAc. The phases were separated, and the EtOAc phase was washed once each with water and brine, dried over $Na_2SO_4$, filtered, and concentrated to an orange oil.

The residue from above was dissolved in 5 mL of isopropanol, 500 mg (1.85 mmol) of the epoxide b (Example 11, part a) was added, and the solution was heated at 78° C. overnight. The mixture was cooled to room temperature, and concentrated under reduced pressure to give an orange oil. The oil was purified by silica gel chromatography, using 50% EtOAc/50% hexanes as eluent, to give 825 mg (66%) of compound I as a white foam. $^1$H NMR (300 MHz, DMSO-d6) δ 9.45 (s, 1H), 8.24 (d, 1H), 8.09 (d, 1H), 7.72 (s, 1H), 7.42–6.77 (m, 25H), 5.09 (s, 2H), 4.49 (m, 1H), 3.67 (m, 2H), 3.61 (s, 3H), 2.50 (m, 6H).

Example 14

Synthesis of N-{2-[4-(4-methoxyphenyl)aminophenyl]ethyl}-2-hydroxy-2-(3-hydroxymethyl-4-hydroxyphenyl)ethylamine (20)

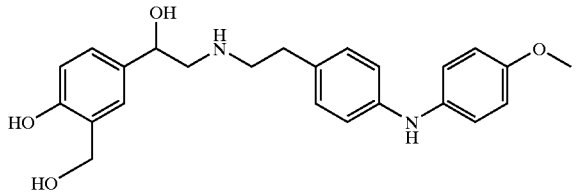

Using a coupling procedure similar to that described in Example 1, except replacing the 4-methoxy-3-phenylaniline hydrochloride with 4-methoxyaniline (p-anisidine), compound 20 was prepared.

Using synthetic methods similar to those described in Examples 1–14, compounds 14–19 and 21–30 are prepared.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A hydrochloride salt of N-{2-[4-(3-phenyl-4-methoxyphenyl)aminophenyl]ethyl}-(R)-2-hydroxy-2-(8-hydroxy-2(1H)-quinolinon-5-yl)ethylamine.

2. A pharmaceutical composition comprising a therapeutically effective amount of the compound of claim 1 and a pharmaceutically-acceptable carrier.

3. The pharmaceutical composition of claim 2, wherein the composition is formulated for administration by inhalation.

4. The pharmaceutical composition of claim 2, wherein the composition further comprises a therapeutically effective amount of a steroidal anti-inflammatory agent.

5. The pharmaceutical composition of claim 2, wherein the composition further comprises a therapeutically effective amount of one or more therapeutic agents selected from the group consisting of a steroidal anti-inflammatory agent, a muscarinic receptor antagonist agent, a phosphodiesterase inhibitor agent, an immunoglobulin antibody, a leukotriene antagonist agent, a cytokine antagonist agent, a protease inhibitor, cromolyn sodium, nedocromil sodium, and sodium cromoglycate.

6. A method of agonizing $\beta_2$ adrenergic receptor activity in a mammal, the method comprising administering to the mammal, a therapeutically effective amount of a pharmaceutical composition of claim 2.

7. The method of claim 6, wherein the disease or condition is a pulmonary disease.

8. The method of claim 7 wherein the pulmonary disease is asthma or chronic obstructive pulmonary disease.

9. The method of claim 6 wherein the disease or condition is selected from the group consisting of pre-term labor, neurological disorders, cardiac disorders, and inflammation.

10. The method of claim 6 further comprising administering a therapeutically effective amount of a steroidal anti-inflammatory agent.

11. The method of claim 6 further comprising administering a therapeutically effective amount of one or more therapeutic agents selected from the group consisting of a steroidal anti-inflammatory agent, a muscarinic receptor antagonist agent, a phosphodiesterase inhibitor agent, an immunoglobulin antibody, a leukotriene antagonist agent, a cytokine antagonist agent, a protease inhibitor, cromolyn sodium, nedocromil sodium, and sodium cromoglycate.

* * * * *